United States Patent

Stein et al.

Patent Number: 5,378,715
Date of Patent: Jan. 3, 1995

[54] SULFONAMIDE ENDOTHELIN ANTAGONISTS

[75] Inventors: Philip D. Stein; John T. Hunt, both of Princeton; Natesan Murugesan, Lawrenceville, all of N.J.

[73] Assignee: Bristol-Myers Squibb Co., Princeton, N.J.

[21] Appl. No.: 92,166

[22] Filed: Jul. 15, 1993

Related U.S. Application Data

[63] Continuation-in-part of Ser. No. 998,246, Jan. 25, 1993, abandoned, which is a continuation-in-part of Ser. No. 840,496, Feb. 24, 1992, abandoned.

[51] Int. Cl.⁶ .................. C07D 261/06; A61K 31/42
[52] U.S. Cl. ...................... 514/329; 514/374; 514/376; 514/377; 514/375; 514/379; 514/380; 546/209; 548/243; 548/244; 548/245; 548/246; 548/241
[58] Field of Search .............. 514/374, 376, 377, 375, 514/329, 379, 380; 548/243, 244, 245, 246, 241, 240; 546/209

[56] References Cited

U.S. PATENT DOCUMENTS

| | | | |
|---|---|---|---|
| 2,888,455 | 5/1959 | Kano et al. | 260/239.9 |
| 4,415,496 | 11/1983 | Harris et al. | 260/239.3 |
| 4,661,479 | 4/1987 | Wyvratt, Jr. et al. | 546/245 |

FOREIGN PATENT DOCUMENTS

| | | | |
|---|---|---|---|
| 76072 | 4/1983 | European Pat. Off. | 546/245 |
| 194548 | 9/1986 | European Pat. Off. | 546/245 |
| 404525 | 12/1990 | European Pat. Off. | 544/278 |
| 443983 | 8/1991 | European Pat. Off. | 260/239.3 |

(List continued on next page.)

OTHER PUBLICATIONS

CA91(25):204438n Efficacy . . . rat. Ritzerfeld, p. 51, 1979.
CA97(11):84685r Renal . . . function. Vree et al., p. 23, 1982.
CA102(23):197512x Pharmacokinetics . . . dosing. Oie, p. 18, 1985.

(List continued on next page.)

Primary Examiner—Mary C. Lee
Assistant Examiner—Joseph K. McKane
Attorney, Agent, or Firm—John M. Kilcoyne

[57] ABSTRACT

Compounds of the formula

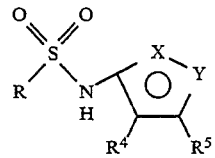

inhibit endothelin, wherein:
one of X and Y is N and the other is O; R is naphthyl or naphthyl substituted with $R^1$, $R^2$ and $R^3$;
$R^1$, $R^2$ and $R^3$ are each independently hydrogen; alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$; halo; hydroxyl; cyano; nitro; —C(O)H; —C(O)$R^6$; CO$_2$H; —CO$_2R^6$; —SH; —S(O)$_nR^6$; —S(O)$_m$—OH; —S(O)$_m$—O$R^6$; —O—S(O)$_m$—$R^6$; —O—S(O)$_m$OH; —O—S(O)$_m$—O$R^6$; —$Z^4$—N$R^7R^8$; or —$Z^4$—N($R^{11}$)—$Z^5$—N$R^9R^{10}$;
$R^4$ and $R^5$ are each independently hydrogen; alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$; halo; hydroxyl; cyano; nitro; —C(O)H; —C(O)$R^6$; —CO$_2$H; —CO$_2R^6$; —SH, —S(O)$_nR^6$; —S(O)$_m$—OH; —S(O)$_m$—O$R^6$; —O—S(O)$_m$—$R^6$; —O—S(O)$_m$OH; —O—S(O)$_m$—O$R^6$; —$Z^4$—N$R^7R^8$; —$Z^4$—N($R^{11}$)—$Z^5$—N$R^9R^{10}$; or $R^4$ and $R^5$ together are alkylene or alkenylene (either of which may be substituted with $Z^1$, $Z^2$ and $Z^3$), completing a 4- to 8-membered saturated, unsaturated or aromatic ring together with the carbon atoms to which they are attached.

20 Claims, No Drawings

FOREIGN PATENT DOCUMENTS

| | | | |
|---|---|---|---|
| 510526 | 10/1992 | European Pat. Off. | 260/239.9 |
| 526708 | 2/1993 | European Pat. Off. | 260/239.3 |
| 804036 | 11/1958 | United Kingdom | 548/243 |
| 1473433 | 5/1977 | United Kingdom | 548/243 |
| 2228933 | 9/1990 | United Kingdom | 546/245 |
| 93/08799 | 5/1993 | WIPO | 548/245 |

OTHER PUBLICATIONS

Derwent Abstract No. 88-289069/41 Feb. 27, 1987.
Derwent Abstract No. 88-195835/28 Nov. 26, 1986.
Derwent Abstract No. 88-061295/09 Jul. 9, 1986.
Derwent Abstract No. 87-152485/22 Oct. 11, 1985.
Derwent Abstract No. 62299 E/30 Dec. 11, 1980.
Derwent Abstract No. 40927 D/23 Sep. 11, 1979.
Derwent Abstract No. 91-254550/35 Feb. 19, 1990.
Derwent Abstract No. 86-246709/38 Nov. 27, 1985.
Derwent Abstract No. 35012 K/15 Sep. 24, 1981.
Allen et al., "Preparation . . . antagonists", CA116(11):106284Z, p. 778, 1992.
R. D. Desai et al., Chemical Abstracts, vol. 71, No. 11, (1969) 49825c.
R. D. Desai et al., Chemical Abstracts, vol. 71, No. 3, (1969) 12872q.

SULFONAMIDE ENDOTHELIN ANTAGONISTS

CROSS-REFERENCE TO RELATED APPLICATION

This is a continuation-in-part of U.S. patent application Ser. No. 998,246, filed Jan. 25, 1993, which in turn is a continuation-in-part of U.S. patent application Ser. No. 840,496, filed Feb. 24, 1992, now abandoned.

FIELD OF THE INVENTION

This invention relates to endothelin antagonists useful, inter alia, for treatment of hypertension.

BRIEF DESCRIPTION OF THE INVENTION

Compounds of the formula

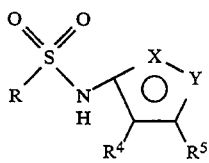

I and pharmaceutically acceptable salts thereof are endothelin receptor antagonists useful, inter alia, as antihypertensive agents. Throughout this specification, the above symbols are defined as follows:

one of X and Y is N and the other is O;

R is naphthyl or naphthyl substituted with $R^1$, $R^2$ and $R^3$;

$R^1$, $R^2$ and $R^3$ are each independently
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
(c) halo;
(d) hydroxyl;
(e) cyano;
(f) nitro;
(g) —C(O)H or —C(O)$R^6$;
(h) —CO$_2$H or —CO$_2R^6$;
(i) —SH, —S(O)$_nR^6$, —S(O)$_m$—OH, —S(O)$_m$—O$R^6$, —O—S(O)$_m$—$R^6$, —O—S(O)$_m$OH, or —O—S(O)$_m$—O$R^6$;
(j) —$Z^4$—N$R^7R^8$; or
(k) —$Z^4$—N($R^{11}$)—$Z^5$—N$R^9R^{10}$;

$R^4$ and $R^5$ are each independently
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
(c) halo;
(d) hydroxyl;
(e) cyano;
(f) nitro;
(g) —C(O)H or —C(O)$R^6$;
(h) —CO$_2$H or —CO$_2R^6$;
(i) —SH, —S(O)$_nR^6$, —S(O)$_m$—OH, —S(O)$_m$—O$R^6$, —O—S(O)$_m$—$R^6$, —O—S(O)$_m$OH, or —O—S(O)$_m$—O$R^6$;
(j) —$Z^4$—N$R^7R^8$;
(k) —$Z^4$—N($R^{11}$)—$Z^5$—N$R^9R^{10}$; or
(l) $R^4$ and $R^5$ together are alkylene or alkenylene (either of which may be substituted with $Z^1$, $Z^2$ and $Z^3$), completing a 4- to 8-membered saturated, unsaturated or aromatic ring together with the carbon atoms to which they are attached;

$R^6$ is alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^7$ is
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
(c) cyano;
(d) hydroxyl;
(e) —C(O)H or —C(O)$R^6$;
(f) —CO$_2$H or —CO$_2R^6$;
(g) —SH, —S(O)$_nR^6$, —S(O)$_m$—OH, —S(O)$_m$—O$R^6$, —O—S(O)$_m$—$R^6$, —O—S(O)$_m$OH, or —O—S(O)$_m$—O$R^6$, except when $Z^4$ is —S(O)$_n$—;

$R^8$ is
(a) hydrogen;
(b) —C(O)H or —C(O)$R^6$, except when $Z^4$ is —C(O)— and $R^7$ is —C(O)H, —C(O)$R^6$, —CO$_2$H, or —CO$_2R^6$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$; or $R^7$ and $R^8$ together are alkylene or alkenylene (either of which may be substituted with $Z^1$, $Z^2$ and $Z^3$), completing a 3- to 8-membered saturated, unsaturated or aromatic ring together with the nitrogen atom to which they are attached;

$R^9$ is
(a) hydrogen;
(b) hydroxyl;
(c) —C(O)H or —C(O)$R^6$;
(d) —CO$_2$H or —CO$_2R^6$;
(e) —SH, —S(O)$_nR^6$, —S(O)$_m$—OH, —S(O)$_m$—O$R^6$, —O—S(O)$_m$—$R^6$, —O—S(O)$_m$OH, or —O—S(O)$_m$—O$R^6$;
(f) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^{10}$ is
(a) hydrogen;
(b) —C(O)H or —C(O)$R^6$, except when $Z^5$ is —C(O)— and $R^9$ is —C(O)H, —C(O)$R^6$, —CO$_2$H, or —CO$_2R^6$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^{11}$ is
(a) hydrogen;
(b) hydroxyl, CO$_2R^6$ or CO$_2$H, except when one of $R^9$ and $R^{10}$ is hydroxyl, CO$_2R^6$ or CO$_2$H;
(c) —C(O)H or —C(O)$R^6$; or
(d) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

or any two of $R^9$, $R^{10}$ and $R^{11}$ together are alkylene or alkenylene (either of which may be substituted with $Z^1$, $Z^2$ and $Z^3$), completing a 3- to 8-membered saturated, unsaturated or aromatic ring together with the atoms to which they are attached;

$Z^1$, $Z^2$ and $Z^3$ are each independently
  (a) hydrogen;
  (b) halo;
  (c) hydroxy;
  (d) alkoxy;
  (e) —SH, —S(O)$_n$Z$^6$, —S(O)$_m$—OH, —S(O)$_m$—OZ$^6$, —O—S(O)$_m$—Z$^6$, —O—S(O)$_m$OH, or —O—S(O)$_m$—OZ$^6$;
  (f) oxo;
  (g) nitro;
  (h) cyano;
  (i) —C(O)H or —C(O)Z$^6$;
  (j) —CO$_2$H or —CO$_2$Z$^6$; or
  (k) —NZ$^7$Z$^8$, —C(O)NZ$^7$Z$^8$, or —S(O)$_n$Z$^7$Z$^8$;

$Z^4$ and $Z^5$ are each independently
  (a) a single bond;
  (b) —S(O)$_n$—;
  (c) —C(O)—;
  (d) —C(S)—; or
  (e) alkyl, alkenyl, alkynyl, cycloalkyl, cycloalkylalkyl, cycloalkenyl, cycloalkenylalkyl, aryl, or aralkyl, any of which may be substituted with $Z^1$, $Z^2$ and $Z_3$;

$Z^6$, $Z^7$ and $Z^8$ are each independently hydrogen, alkyl, alkenyl, alkynyl, cycloalkyl, cycloalkylalkyl, cycloalkenyl, cycloalkenylalkyl, aryl, or aralkyl, or $Z^7$ and $Z^8$ together are alkylene or alkenylene, completing a 3- to 8-membered saturated, unsaturated or aromatic ring together with the nitrogen atom to which they are attached;

m is 1 or 2; and
n is 0, 1, or 2.

For compound I, it is preferred that:
R is

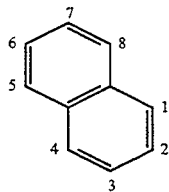

with the sulfonamide attached at position 1 or 2 and one of $R^1$, $R^2$ and $R^3$ attached at position 5 or 6;
one of $R^1$, $R^2$ and $R^3$ is —NR$^7$R$^8$;
$R^4$ and $R^5$ are alkyl;
$R^7$ and $R^8$ are each independently hydrogen, alkyl, or —C(O)R$^6$ wherein $R^6$ is alkyl.

Most preferred are compounds wherein one of $R^1$, $R^2$ and $R^3$ is —NR$^7$R$^8$ and the other two are hydrogen, —NR$^7$R$^8$ is attached at position 5 and the sulfonamide is attached at position 1, $R^4$ and $R^5$ are methyl, and $R^7$ and $R^8$ are hydrogen, methyl, methylethyl, or acetyl.

DETAILED DESCRIPTION OF THE INVENTION

Listed below are definitions of terms used in this specification. These definitions apply to the terms as used throughout this specification, individually or as part of another group, unless otherwise limited in specific instances.

The terms "alkyl" and "alkoxy" refer to straight or branched chain hydrocarbon groups having 1 to 10 carbon atoms. The terms "lower alkyl" and "lower alkoxy" refer to groups of 1 to 4 carbon atoms, which are preferred.

The term "aryl" or "ar-" refers to phenyl, naphthyl, and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH$_2$)$_m$— wherein m is 1 to 5), which may be substituted with 1 to 3 lower alkyl groups.

The term "alkenylene" refers to a straight chain bridge of 1 to 5 carbon atoms having one or two double bonds that is connected by single bonds (e.g., —CH=CH$_2$—CH=CH—, —CH$_2$—CH=CH—, —CH$_2$—CH=CH—CH$_2$—) which may be substituted with 1 to 3 lower alkyl groups.

The terms "cycloalkyl" and "cycloalkenyl" refer to cyclic hydrocarbon groups of 3 to 8 carbon atoms.

The term "aralkyl" refers to an alkyl group substituted by one or more aryl groups.

The terms "halogen" and "halo" refer to fluorine, chlorine, bromine and iodine.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, benzathine, N-methyl-D-glucamide and hydrabamine and with amino acids such as arginine, lysine and the like. Such salts may be obtained by reacting compound I with the desired ion in a medium in which the salt precipitates or in an aqueous medium followed by lyophilization.

When the $R^1$ to $R^5$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate, and various other sulfonates, nitrates, phosphates, borates, acetates, tartrates, maleates, citrates, succinates, benzoates, ascorbates, salicylates, and the like. Such salts may be formed by reacting compound I in an equivalent amount of the acid in a medium in which the salt precipitates or in an aqueous medium followed by lyophilization.

In addition, when the $R^1$ to $R^5$ substituents comprise a basic moiety such as amino, zwitterions ("inner salts") may be formed.

Certain of the $R^1$ to $R^5$ substituents of compound I may contain asymmetric carbon atoms. Such compounds of formula I may exist, therefore, in enantiomeric and diasteromeric forms and in racemic mixtures thereof. All are within the scope of this invention.

The compounds of formula I are antagonists of ET-1, ET-2, and/or ET-3 and are useful in treatment of all endothelin-dependent disorders. They are thus useful as antihypertensive agents. By the administration of a composition having one (or a combination) of the compounds of this invention, the blood pressure of a hypertensive mammalian (e.g., human) host is reduced.

The compounds of the present invention are also useful in the treatment of disorders related to renal, glomerular, and mesangial cell function, including chronic renal failure, glomerular injury, renal damage secondary to old age, nephrosclerosis (especially hypertensive nephrosclerosis), nephrotoxicity (including nephrotoxicity related to imaging and contrast agents), and the like. The compounds of this invention may also be useful in the treatment of disorders related to paracrine and endocrine function.

The compounds of the present invention are also useful in the treatment of endotoxemia or endotoxin shock.

The compounds of the present invention are also useful as anti-ischemic agents for the treatment of, for example, heart, renal and cerebral ischemia and the like.

In addition, the compounds of this invention may also be useful as anti-arrhythmic agents; anti-anginal agents; anti-fibrillatory agents; anti-asthmatic agents; therapy for myocardial infarction; therapy for peripheral vascular disease (e.g., Raynaud's disease); anti-atherosclerotic agents; treatment of cardiac hypertrophy (e.g., hypertrophic cardiomyopathy); treatment of pulmonary hypertension; additives to cardioplegic solutions for cardiopulmonary bypasses; adjuncts to thrombolytic therapy; treatment of central nervous system vascular disorders: for example, as anti-stroke agents, anti-migraine agents, and therapy for subarachnoid hemorrhage; treatment of central nervous system behavioral disorders; anti-diarrheal agents; regulation of cell growth; and treatment of hepatoxicity and sudden death.

The compounds of this invention can also be formulated in combination with endothelin converting enzyme (ECE) inhibitors, such as phosphoramidon; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril, and salts of such compounds; neutral endopeptidase (NEP) inhibitors; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories). If formulated as a fixed dose, such combination products employ the compounds of this invention within the dosage range described below and the other pharmaceutically active agent within its approved dosage range. The compounds of this invention may also be formulated with or useful in conjunction with antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

A sulfonyl halide

$$R\text{—}SO_2halo \qquad \qquad II$$

is coupled with an isoxazolamine

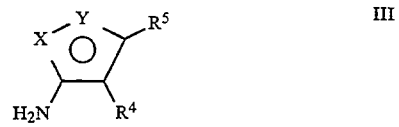

III in an anhydrous organic solvent (e.g., pyridine) to form compound I.

Alternatively, a sulfonamide

$$R\text{—}SO_2NH_2 \qquad \qquad IIa$$

is coupled with

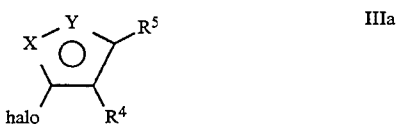

IIIa in an anhydrous organic solvent in the presence of a base (e.g., $Cs_2CO_3$) to form compound 1.

For compounds wherein any of $R^1$ to $R^5$ comprise reactive functionalities, the reactants may be treated with protecting agents prior to coupling. Suitable protecting agents and procedures for use thereof are generally known in the art. Exemplary protecting groups are benzyl, halocarbobenzyloxy, tosyl and the like for hydroxyl; carbobenzyloxy, halocarbobenzyloxy, acetyl, benzoyl and the like for amino. Such groups may then be removed from the resulting protected analogue of compound I by treatment with one or more deprotecting agents. Suitable deprotecting agents and procedures for use thereof are generally known in the art.

To form compound I wherein one or more of $R^1$ to $R^3$ is $-NR^7R^8$ and/or $R^8$ is acyl, the associated nonacyl sulfonic acid

R—SO₃H                                IV is treated with water and an alkali metal hydroxide (e.g., sodium hydroxide) to form a sulfonic acid salt

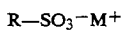
R—SO₃⁻M⁺                              V wherein $M^+$ is a lithium, sodium or potassium ion. Salt V is treated with an acylating agent (e.g., acetic anhydride) at about 90° to 110° C. in either the acylating agent as solvent or in an anhydrous organic solvent (e.g., pyridine) to form a sulfonic acid salt of formula V wherein one or more $R^1$, $R^2$ and $R^3$ is $-NR^7R^8$ and at least one of $R^7$ and $R^8$ is acyl. Sulfonic acid salt V is then treated with a halosulfonic acid solution (e.g., chlorosulfonic acid) or with another chlorinating agent (e.g., phosphorus pentachloride, thionyl chloride) at about 0° C. to 80° C. to form an acyl-sulfonic halide of formula II, which is coupled with isoxazolamine III as described above to form compound I wherein at least one of $R^1$, $R^2$ and $R^3$ is $-NR^7R^8$ and at least one of $R^7$ and $R^8$ is acyl.

Substituted amines of formula I (e.g., compounds having $-NR^7R^8$ wherein at least one of $R^7$ and $R^8$ is other than hydrogen) can be prepared from the associated free amine (wherein $R^7$ and $R^8$ are hydrogen). The free amine is treated with (1) a ketone or aldehyde (e.g., acetone), (2) a reducing agent (e.g., sodium cyanoborohydride) or hydrogen gas ($H_2$) and a catalyst (e.g., palladium on carbon), and (3) an acid (e.g., acetic acid, hydrochloric acid) in an organic solvent (e.g., methanol) to form the associated monoamine compound I (e.g., Examples 18, 25 hereinafter).

The nitrogen atom of the sulfonamide core may need to be protected during this process (see, e.g., Example 38). Suitable protecting groups are generally known in the art. The protecting group may be added by treating the free amine with the halide of the protecting group at about 0° C. in the presence of a base (e.g., triethylamine). After addition of the $R^7$ or $R^8$ group as described above, the protecting group may be removed by treatment with an acid (e.g., trifluoroacetic acid) in an organic solvent (e. g., methylene chloride) at about 0° C.

Alternatively, the substituted amine may be prepared from the associated acyl compound (prepared as described above) by treatment with a reducing agent such as borane.

Compounds of formula I having cyclized amine substituents (e.g., compounds wherein $R^7$ and $R^8$ together are alkylene or alkenylene) may be formed as follows. The associated free amine undergoes reductive amination by treatment with an aldehyde or ketone halide (e.g., 4-chlorobutanal) in an organic solvent (e.g., methylene chloride) at about 20° to 30° C. to form a compound of the formula

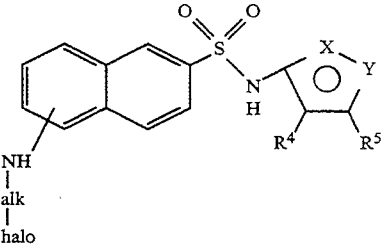

wherein "alk" is alkylene or alkenylene and "halo" is a halogen atom. When the alk group is substituted with an oxo group at the carbon adjacent to the amino group, an acid halide (e.g., 4-bromobutyryl chloride) is used instead of the aldehyde in the presence of a base (e.g., pyridine). Compound VI is then cyclized by treatment with a base (e.g., cesium carbonate) in an organic solvent (e.g., dimethylformamide) at about 55° to 65° C. to form compound I wherein $R^7$ and R8 together are alkylene or alkenylene.

Compounds of formula I having cyclized amine substituents may also be prepared by the following alternative process. The associated free amine undergoes reductive amination by treatment with a diketone or dialdehyde (e.g., glutaric dialdehyde)in the presence of an organic acid (e.g., acetic acid) in an organic solvent (e.g., dioxane), followed by a reducing agent (e.g., sodium cyanoborohydride) to form the cyclized amine wherein $R^7$ and $R^8$ together are alkylene or alkenylene.

The associated free amine (having $-NR^7R^8$ wherein $R^7$ and $R^8$ are both hydrogen) may also be condensed with a compound of the formula

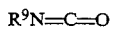
$R^9N=C=O$                            VIIa or a compound of the formula

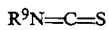
$R^9N=C=S$                            VIIb wherein $R^9$ in compounds VIIa and VIIb is selected from subparagraph (f) in its foregoing definition (e.g., wherein compound VIIb is phenylisothiocyanate). This reaction can take place in the presence of a base (e.g., triethylamine) and a catalyst (e.g., dimethylaminopyridine) in an organic solvent (e.g., acetone) at about 60° to 70° C. to form compound I wherein one of $R^1$ to $R^5$ is $-Z^4-N(R^{11})-Z^5-NR^9R^{10}$.

To form compound I wherein one or more of $R^1$ to $R^3$ is alkoxy, the associated hydroxy sulfonic acid IV may be treated with an alkylating agent (e.g., dimethylsulfate) and an alkali metal hydroxide (e.g., sodium hydroxide) in an aqueous/organic solvent mixture (e.g., water/ethanol), followed by an acid (e.g., hydrochloric acid). The resulting alkoxy sulfonic acid salt V may be used as described above to form compound I.

For compounds wherein one of $R^1$ to $R^5$ comprises an acid moiety, the associated ester (e.g., wherein $R^1$ is $-CO_2R^6$ or alkyl substituted with $-CO_2Z^6$) is formed by coupling compounds II and III as described above, followed by deesterifying with, for example, sodium hydroxide in an alcohol such as methanol at about 20° to 30° C.

Compounds wherein one of $R^1$ to $R^5$ comprises a hydroxyl moiety (e.g., wherein $R^1$ is hydroxyl or alkyl substituted with hydroxyl) may be prepared by reducing the associated carboxylic acid; for example, by treatment with borane in an organic solvent (e.g., tetrahydrofuran) at about 0° to 30° C. Alternatively, the associated ester may be treated with an organometallic reagent (e.g., methyl magnesium bromide) in an organic solvent (e.g., tetrahydrofuran) with heating to reflux to form the hydroxyl compound. In a further alternative, the protected hydroxyl formed by coupling of compounds II and III may be conventionally deprotected as described above.

Compounds wherein one of $R^1$ to $R^5$ comprises an alkenyl moiety may be prepared by eliminating water from the associated hydroxyl compound; for example, by treatment with an acid (e.g., trifluoroacetic acid) in an organic solvent (e.g., methylene chloride) with heating to reflux.

Compounds wherein one of $R^1$ to $R^3$ comprises a keto or aldehyde moiety may be prepared from the associated alcohol by treatment with an oxidizing agent (e.g., pyridinium chlorochromate) in an organic solvent (e.g., methylene chloride) at about 20° to 30° C.

Such aldehydes may be reductively aminated to form disubstituted amines of compound I. For example, the aldehyde is treated with an acid (e.g., acetic acid), a disubstituted amine (e.g., dimethylamine) and a reducing agent (e.g., triacetoxyborohydride) in an organic solvent (e.g., tetrahydrofuran) to form a disubstituted amine of formula I.

The invention will now be further described by the following working examples, which are preferred embodiments of the invention. In the following structures, "Ac" stands for acetyl, "Me" for methyl. These examples are meant to be illustrative rather than limiting.

EXAMPLE 1

5-(Dimethylamino)-N-(3,4-dimethyl-5-isoxazolyl)-1-naphthalenesulfonamide

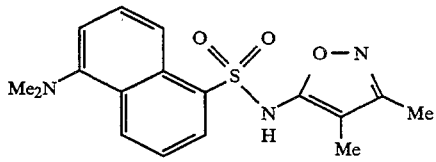

A solution of dansyl chloride (2.07 g, 7.67 mmol) in pyridine (10 mL) was added dropwise to a solution of 3,4-dimethyl-5-isoxazolamine (1.65 g, 14.7 mmol) in pyridine (5 mL). The reaction mixture was heated at 60° C. overnight. After cooling to room temperature, the reaction mixture was added dropwise to water (100 mL) and the suspension was stirred overnight, forming a yellowish-brown gum. The water was decanted, and the gum was dissolved in ether (50 mL) and extracted with water (50 mL). The ether layer was evaporated to leave a fluffy yellow solid that was dried under vacuum to yield 1.41 g (55%). The product was passed through a column of silica using 15% ethyl acetate/methylene chloride as the solvent. Fractions containing product were combined and evaporated to provide 0.84 g of Example 1 as an amorphous yellow solid.

Melting point: 126.2° to 129.8° C.

EXAMPLE b 2

N-[5-[[(3,4-Dimethyl-5-isoxazolyl)amino]sulfonyl]-1-naphthalenyl]acetamide

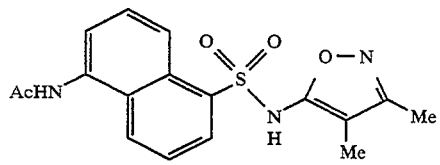

A. 5-Amino-1-naphthalenesulfonic acid, sodium salt

To a suspension of 5-amino-1-naphthalenesulfonic acid (12 g, 54 mmol) in water (130 mL) was added 5N sodium hydroxide (11 mL). After 5 minutes, the water was removed in vacuo and the residue washed with toluene (20 mL) to yield 13.0 g (98%) of compound A.

B. 5-(Acetylamino)-1-naphthalenesulfonic acid, sodium salt

Acetic anhydride (50 mL) was added to compound A (13.0 g, 53.0 mmol), and the suspension was heated at 100° C. for 1.5 hours. After cooling to room temperature, the product was vacuum-filtered, washed with ethanol (100 mL), and dried under vacuum to yield 14.8 g (97%) of compound B, which was then further dried in a vacuum oven (40° C.).

C. N-[5-(Chlorosulfonyl)-1-naphthalenyl]acetamide

A solution of compound B (2.67 g, 9.29 mmol) in chlorosulfonic acid (12 mL) was stirred at room temperature for 2.5 hours. The reaction mixture was dropped very slowly into crushed ice (150 mL) and the suspension was stirred until the ice melted, leaving a fine precipitate which was vacuum-filtered and dried to yield 2.63 g (100%) of compound C.

D. N-[5-[[(3,4-Dimethyl-5-isoxazolyl)-amino]sulfonyl]-1-naphthalenyl]acetamide

To a solution of 3,4-dimethyl-5-isoxazolamine (1.21 g, 10.8 mmol) in pyridine (7 mL) was added a solution of compound C (1.51 g, 5.32 mmol) in pyridine (13 mL), dropwise over a 10 minute period. The reaction mixture was heated at 70° C. for 2 hours. After cooling to room temperature, most of the pyridine was removed in vacuo and the residue was diluted to 50 mL with water. Upon acidification to pH 3 with 6N hydrochloric acid, a precipitate formed which was vacuum-filtered and dried to yield 0.36 g (19%) of Example 2. Recrystallization of 0.19 g from ethanol/water afforded 0.12 g of brown crystals. Melting point: 216.3° to 222.0° C.

EXAMPLE 3

5-Amino-N-(3,4-dimethyl-5-isoxazolyl)-1-naphthalenesulfonamide

A solution of Example 2 (0.188 g, 0.523 mmol) in 5N sodium hydroxide (2 mL) and methanol (1 mL) was heated at 70° C. overnight. After cooling to room temperature, the reaction mixture was acidified to pH 3 with 1N hydrochloric acid, forming a precipitate which was filtered and dried in vacuo to yield 0.14 g (84%). Recrystallization from ethanol/water afforded dark orange crystals (0.084 g, 51%).

Melting point: 121.5° to 127.0° C.

EXAMPLE 4

N-[6-[[(3,4-dimethyl-5-isoxazolyl)amino]sulfonyl]-1-naphthalenyl]acetamide

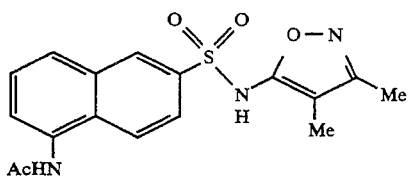

A. Sodium 5-amino-2-naphthalenesulfonate

To a suspension of 5-amino-2-naphthalene sulfonic acid (25 g, 0.11 mol) in water (300 mL) was added 5N sodium hydroxide (23 mL). After the solution stirred 5 minutes, the water was removed in vacuo, and the residue was washed with toluene (50 mL) and dried under vacuum to yield 27.9 g (100%) of compound A.

B. Sodium 5-acetylamino-2-naphthalenesulfonate

A suspension of compound A (14.6 g, 59.6 mmol) in acetic anhydride (80 mL) was heated at 100° C. for 3 hours. After cooling to room temperature the mixture was vacuum-filtered and the solid was washed with ethanol. The solid was stirred in ethanol (100 mL) for 5 minutes, re-filtered and dried to yield 15.7 g (92%) of compound B.

C. 5-Acetylamino-2-naphthalenesulfonyl chloride

In a large mortar were ground compound B (7.00 g, 24.4 mmol) and phosphorus pentachloride (10.1 g, 48.7 mmol) to form a thick, brown bubbling liquid. This mixture was allowed to sit for 15 minutes and then ground with crushed ice (400 g). After the ice melted, the resulting fine powdery precipitate was vacuum-filtered and extracted in a Soxhlet extractor with ethyl acetate for 3 hours. Concentration of the ethyl acetate solution yielded 6.39 g (92%) of compound C.

D. N-[6-[[(3,4-dimethyl-5-isoxazolyl)amino]sulfonyl]-1-naphthalenyl]acetamide

To a solution of 3,4-dimethyl-5-isoxazolamine (1.74 g, 15.5 mmol) in pyridine (8 mL) was added compound C (4.02 g, 14.2 mmol) all at once with stirring. The reaction mixture turned brown and was allowed to stir overnight at room temperature and then at 75° C. for 1 hour. The product was precipitated by adjusting the reaction mixture to pH 3 with 6N hydrochloric acid and collected by vacuum filtration to yield 2.36 g (47%) of the title compound in crude form. This material was recrystallized from ethanol/chloroform to yield 0.263 g (5%) of Example 4 as a pink powder.

Melting point: 210.5°–212.0° C. Analysis for $C_{17}H_{17}N_3O_4S$.00.31 $H_2O$ Calc'd: C, 55.95; H, 4.87; N, 11.51; S, 8.78. Found: C, 55.95; H, 4.68; N, 11.41; S, 8.71.

EXAMPLE 5

5-Amino-N-(3,4-dimethyl-5-isoxazolyl)-2-naphthalenesulfonamide

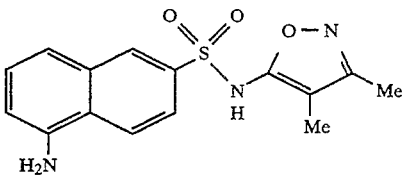

A stirred solution of Example 4 (1.36 g, 3.78 mmol), sodium hydroxide (5N, 4.5 mL), water (1.5 mL), and methanol (1 mL) was heated at 60° C. overnight. After cooling to room temperature, the reaction mixture was diluted up to 40 mL with water and acidified to pH 3 with 6N hydrochloric acid to afford a brown precipitate. Upon stirring, the solid became a powder which was then vacuum filtered and dried. Recrystallization from toluene afforded 0.113 g (9%) of pure Example 5 as a yellow powder.

Melting point: 152.5°–153.8° C. Analysis for $C_{15}H_{15}N_3O_3S$ Calc'd: C, 56.77; H, 4.76; N, 13.24; S, 10.10. Found: C, 56.93; H, 4.75; N, 13.12; S, 10.18.

EXAMPLE 6

N-[4-[[(3,4-Dimethyl-5-isoxazolyl)amino]sulfonyl]-1-naphthalenyl]acetamide

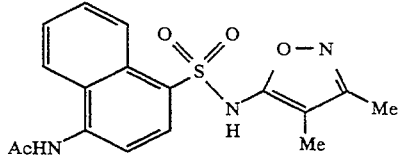

A. 4-Acetylamino-1-naphthalenesulfonyl chloride

In a large mortar, sodium 4-acetylamino-1-naphthalenesulfonate (3.00 g, 10.4 mmol) was ground with phosphorus pentachloride (3.80 g, 18.2 mmol) to form a bubbling paste which soon became dry. After standing for 1 hour at room temperature, the mixture was added to crushed ice (150 mL). After the ice mixture was ground in the mortar, it was stirred until the ice melted, leaving a pink, powdery precipitate which was vacuum-filtered and dried to yield 1.07 g (36%) of compound A.

B. N-[4-[[(3,4-Dimethyl-5-isoxazolyl)amino]sulfonyl]-1-naphthalenyl]acetamide

To a solution of 3,4-dimethyl-5-isoxazolamine (0.217 g, 1.94 mmol) in pyridine (2 mL) was added compound A (0.503 g, 1.77 mmol). The reaction mixture turned brown and warmed slightly. After stirring 4.5 hours, the mixture was added dropwise to water (30 mL) to form a white precipitate, which was removed by vacuum filtration. The filtrate was acidified to pH 3 with 6N hydrochloric acid and the precipitate was collected and dried (0.216 g, 33%). Recrystallization of the solid from ethanol/water yielded 0.12 g (18%) of Example 6 as dark red crystals.

Melting point: 199.3°–205.5° C. Analysis for $C_{17}H_{17}N_3O_4S$.0.2 $H_2O$ Calc'd: C, 56.24; H, 4.83; N, 11.57; S, 8.83. Found: C, 56.42; H, 4.60; N, 11.39; S, 8.96.

EXAMPLE 7

N-[6-[[(3,4-Dimethyl-5-isoxazolyl)amino]sulfonyl]-2-naphthalenyl]acetamide

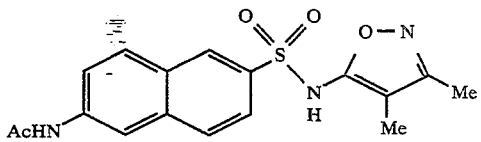

A. Sodium 6-amino-2-naphthalenesulfonate

To a stirred suspension of 6-amino-2-naphthalenesulfonic acid (3.01 g, 13.5 mmol) in methanol (100 mL) was added 5N sodium hydroxide (2.7 mL). The reaction mixture was stirred for 5 minutes, the methanol was removed in vacuo and the residue dried to yield 2.44 g (74%) of compound A.

B. Sodium 6-acetylamino-2-naphthalenesulfonate

A suspension of compound A (2.44 g, 9.95 mmol) in acetic anhydride (15 mL) was heated at 100° C. for 1 hour. The product was vacuum-filtered, washed with ethanol (100 mL) and dried to yield compound B (2.52 g, 88%).

C. 6-Acetylamino-2-naphthalenesulfonyl chloride

Chlorosulfonic acid (7 mL) was added to compound B (2.41 g, 8.39 mmol), and the dark brown solution was allowed to stand at room temperature for 2.5 hours. The reaction mixture was then added dropwise to crushed ice (100 mL) and stirred until the ice melted. The precipitate was vacuum-filtered, washed with water, and dried to afford 2.38 g (100%) of compound C.

D. N-[6-[[(3,4-Dimethyl-5-isoxazolyl)-amino]sulfonyl]-2-naphthalenyl]acetamide

A solution of compound C (2.36 g, 8.32 mmol) in pyridine (20 mL) was added dropwise to a stirred solution of 3,4-dimethyl-5-isoxazolamine (1.91 g, 17.0 mmol) in pyridine (5 mL), and the reaction mixture was heated at 70° C. for 4 hours. After cooling to room temperature, the mixture was added dropwise to water (100 mL) and the aqueous solution was acidified to pH 3 with 6N hydrochloric acid, forming a sandy brown precipitate which was vacuum-filtered and dried. Recrystallization from methanol/water afforded pure Example 7 as fine, tan crystals (0.342 g, 11%).

Melting point: 206.2°-207.0° C. Analysis for $C_{17}H_{17}N_3O_4S \cdot 0.15\ H_2O$ Calc'd: C, 56.39; H, 4.82; N, 11.60; S, 8.85 Found: C, 56.57; H, 4.60; N, 11.42; S, 9.04.

EXAMPLE 8

6-Amino-N-(3,4-dimethyl-5-isoxazolyl)-2-naphthalenesulfonamide

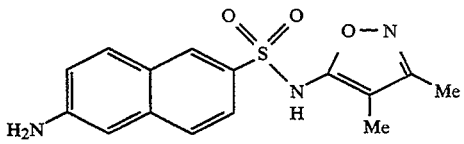

A stirred solution of Example 7 (0.216 g, 0.601 mmol) in 5N sodium hydroxide (1.4 mL) and methanol (1 mL) was heated at 70° C. overnight. After the reaction mixture cooled to room temperature, the pH was brought to about 2 to 3 with hydrochloric acid (1N). The pale pink precipitate that formed was filtered and dried in vacuo to yield 0.174 g (91%). Recrystallization from ethanol/water afforded 0.145 g (71%) of Example 8 as small beige crystals.

Melting point: 174.5°-176.0° C. Analysis for $C_{15}H_{15}N_3O_3S \cdot 0.17\ H_2O$ Calc'd: C, 56.22; H, 4.83; N, 13.11; S, 10.01. Found: C, 56.32; H, 4.65; N, 13.02; S, 9.88.

EXAMPLE 9

4-Amino-N-(3,4-dimethyl-5-isoxazolyl)-1-naphthalenesulfonamide

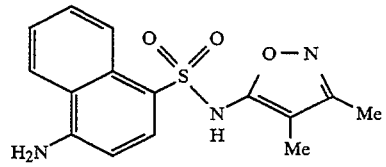

A mixture of Example 6 (200 mg, 0.557 mmol) and 5N sodium hydroxide (1 mL) was heated at 70° C. for 2 hours. After cooling, the reaction was acidified with 6N hydrochloric acid to pH 2. The precipitate was collected by filtration, washed with water (2×2 mL) and dried.

The crude material was suspended in toluene (about 10 mL) and brought to a boil. Ethanol was added to the boiling mixture to effect solubilization. Continued boiling resulted in the formation of a small amount of a purple precipitate. The precipitate was removed by hot filtration and the flitrate was immediately cooled in ice. The solid product which formed was collected by filtration, washed with toluene and dried. This material was triturated with ether (5 mL) and washed with ether (2×2 mL) and dried to yield pure Example 9 (52 mg, 29%) as a tan powder.

Melting point: 152.0°-154.0° C.; Analysis for $C_{15}H_{15}N_3O_3S \cdot 0.20\ H_2O$ Calc'd: C, 56.13; H, 4.84; N, 13.09. Found: C, 56.15; H, 4.53; N, 12.85.

EXAMPLE 10

5-Dimethylamino-N-(4,5-dimethyl-3-isoxazolyl)-1-naphthalenesulfonamide

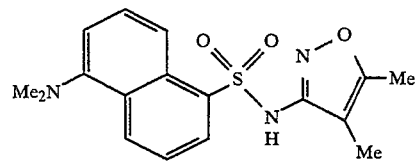

To a solution of 4,5-dimethyl-3-isoxazolamine (135 mg, 1.20 mmol) in pyridine (2 mL) was added 5-dimethylamino-1-naphthalenesulfonyl chloride (270 mg, 1.00 mmol) in one portion. After stirring for 2 hours, the reaction was added to water (20 mL) dropwise. The mixture was brought to pH 8.5 with 2N sodium hydroxide. The mixture was filtered through Celite ® and the filtrate was then brought to pH 4. The resultant gum was stirred for 1 hour and the precipitate was collected by filtration, washed with water (3×10 mL) and dried in vacuo. The yellowish powder (252.9 mg) was recrystallized from 95% ethanol (about 2 mL) after a hot filtration step. The crystalline material was collected, rinsed with cold ethanol (1 mL) and dried to yield 250 mg (72%) of Example 10 as light green crystals.

Melting point: 190.5°–192.0° C. Analysis for $C_{17}H_{19}N_3O_3S$ Calc'd: C, 59.11; H, 5.54; N, 12.17; S, 9.28. Found: C, 59.15; H, 5.50; N, 12.08; S, 9.38.

EXAMPLE 11

N-[5-[[(4,5-dimethyl-3-isoxazolyl)amino]sulfonyl]-1-naphthalenyl]acetamide

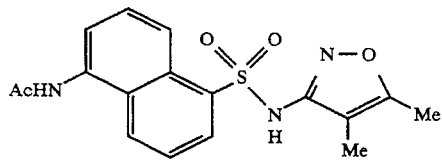

To a solution of 4,5-dimethyl-3-isoxazolamine (123 mg, 1.10 mmol) in pyridine (1 mL) was added 5-acetylamino-1-naphthalenesulfonyl chloride (284 mg, 1.00 mmol) in one portion. The reaction was stirred for 1 hour and was then added dropwise to water (20 mL). The pH of the solution was adjusted to 7.5 with 2N sodium hydroxide. A small amount of a precipitate was removed by filtration. The flitrate was brought to pH 2.5 with 6N hydrochloric acid. The brown precipitate was collected by filtration, washed with water (2×10 mL) and dried. This material (239 mg) was recrystallized from ethanol/water to yield Example 11 (139 mg, 39%) as a brown crystals.

Melting point: 225.0°–226.0° C. Analysis for $C_{17}H_{17}N_3O_4S$ Calc'd: C, 56.81; H, 4.77; N, 11.69; S, 8.92. Found: C, 56.63; H, 4.61; N, 11.50; S, 9.14.

EXAMPLE 12

N-[5-[[(3,4-dimethyl-5-isoxazolyl)amino]sulfonyl]-2-naphthalenyl]acetamide

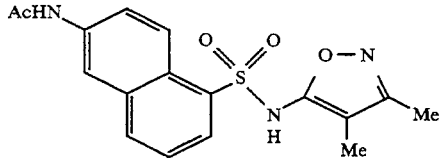

A. 6-Amino-1-napthalenesulfonic acid, sodium salt

To a suspension of 6-amino-1-napthalene-sulfonic acid (10.0 g, 44.8 mmol) in water (10 mL) was added 5N sodium hydroxide (9 mL, 45 mmol). The mixture was warmed to effect complete solution, and then the solvent was removed in vacuo to provide compound A as a white solid (11.3 g).

B. 6-Acetylamino-1-napthalenesulfonic acid, sodium salt

Compound A (10.0 g, 40.8 mmol) was suspended in acetic anhydride (100 mL). The mixture was heated at 95° C. for 4 hours, cooled to room temperature and concentrated in vacuo to provide 11.2 g of compound B as a white powder.

C. 6-Acetylamino-1-naphthalenesulfonyl chloride

A solution of compound B (1.00 g, 3.48 mmol) in chlorosulfonic acid (5.0 mL, 75.2 mmol) was stirred at room temperature under argon for 2.5 hours. The reaction was then added dropwise to about 400 mL of crushed ice, and the mixture was allowed to stir until all of the ice melted. A fine precipitate formed which was vacuum-filtered, washed with copious amounts of water (400 mL), and dried to yield compound C (0.850 g, 86%).

D. N-[5-[[(3,4-dimethyl-5-isoxazolyl)amino]sulfonyl]-2-naphthalenyl]acetamide

A solution of compound C (0.700 g, 2.47 mmol) in pyridine (3 mL) was added dropwise to a solution of 3,4-dimethyl-5-isoxazolamine (0.358 g, 3.19 mmol) and dimethylaminopyridine (0.057 g, 0.467 mmol) in pyridine (3 mL). The reaction was heated at 70° C. for 6 hours, then cooled to room temperature. The solution was added dropwise to water (100 mL) and upon acidification to pH 3 with 6N hydrochloric acid a white solid precipitated which was collected by filtration and dried to a solid (0.713 g, 80%). Recrystallization of 0.200 g of the solid from methanol/water afforded Example 12 as light brown crystals (0.140 g, 56%).

Melting point: 232.2°–235.5° C. (decomp.). Analysis for $C_{17}H_{17}N_3O_4S \cdot 0.01\ H_2O$ Calc'd: C, 56.79; H, 4.77; N, 11.69; S, 8.92. Found: C, 56.77; H, 4.65; N, 11.71; S, 9.05.

EXAMPLE 13

N-[8-[[(3,4-dimethyl-5-isoxazolyl)amino]sulfonyl]-2-naphthalenyl]acetamide

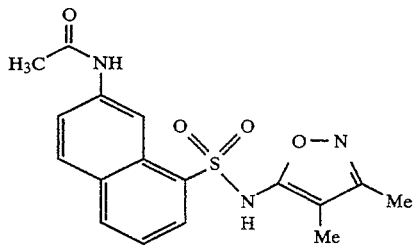

A. Sodium 7-amino-1-naphthalenesulfonate

To a suspension of 7-amino-1-napthalenesulfonic acid (10.0 g, 44.8 mmol) in water (10 mL) was added sodium hydroxide (5N, 9 mL, 45 mmol). The resultant solution was concentrated in vacuo to yield compound A as a solid (11.0 g).

B. Sodium 7-acetylamino-1-naphthalenesulfonate

A portion of compound A (10.0 g, 40.8 mmol) was suspended in acetic anhydride (125 mL). This mixture was heated at 95° C. for 6 hours, cooled and concentrated in vacuo to provide compound B as a tan powder (11.8 g, 100%).

C. 7-Acetylamino-1-naphthalenesulfonyl chloride

Compound B (1.00 g, 3.48 mmol) was added in portions to chlorosulfonic acid (3 mL) held at 0° C. The mixture was brought to room temperature and stirred for 1 hour. The reaction was carefully added to crushed ice (30 g). The mixture was stirred until the ice had melted and then the precipitate was collected by filtration, washed with water (4×15 mL) and dried in vacuo to yield 893 mg (90%) of compound C.

D. N-[8-[[(3,4-dimethyl-5-isoxazolyl)amino]sulfonyl]-2-naphthalenyl]acetamide

To a solution of 3,4-dimethyl-5-isoxazolamine (206 mg, 1.83 mmol) and 4-dimethylaminopyridine (35 mg) in pyridine (2 mL) was added compound C (400 mg, 1.41 mmol). The mixture was heated to 75° C. for 5 hours. The reaction mixture was cooled to room temperature, poured into water (30 mL) and brought to pH 1.5 with 6N hydrochloric acid. The sticky mixture was stirred for 2 days. The resultant precipitate was collected by filtration, washed with water (3×10 mL) and dried in vacuo. Recrystallization of this material from ethanol/water yielded Example 13 (319 mg, 63% yield) as tan crystals.

Melting point: 140.0°–143.0° C.

EXAMPLE 14

N-[7-[[(3,4-dimethyl-5-isoxazolyl)amino]sulfonyl]-2-naphthalenyl]acetamide

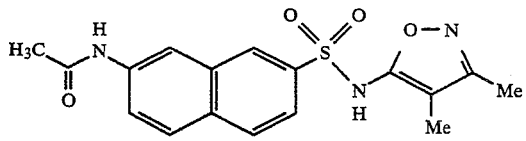

A. Sodium 7-acetylamino-2-naphthalenesulfonate

Sodium 7-amino-2-naphthalenesulfonate (13.2 g, containing 24% sodium chloride and 10% water, 40.8 mmol) was suspended in acetic anhydride (100 mL). This mixture was heated at 95° C. for 4 hours, cooled and concentrated in vacuo to provide compound A as a tan powder (13.4 g, 90%).

B. 7-Acetylamino-2-naphthalenesulfonyl chloride

Compound A (1.33 g, contains 25% sodium chloride, 3.48 mmol) was added in portions to chlorosulfonic acid (3 mL) held at 0° C. The mixture was brought to room temperature and stirred for 4 hours. The reaction was carefully added to crushed ice (30 g). The mixture was stirred until the ice had melted and then the precipitate was collected by filtration, washed with water (4×15 mL) and dried in vacuo to yield 651 mg (66%) of compound B.

C. N-[7-[[(3,4-dimethyl-5-isoxazolyl)amino]sulfonyl]-2-naphthalenyl]acetamide

To a solution of 3,4-dimethyl-5-isoxazolamine (206 mg, 1.83 mmol) and 4-dimethylaminopyridine (35 mg) in pyridine (2 mL) was added compound B (400 mg, 1.41 mmol). The mixture was heated to 75° C. for 4 hours. The reaction mixture was cooled to room temperature, poured into water (30 mL) and brought to pH 1.5 with 6N hydrochloric acid. The sticky mixture was stirred for 17 h. The resultant precipitate was collected by filtration, washed with water (3×10 mL) and dried in vacuo. Recrystallization of this material from ethanol/water yielded Example 14 (324 mg, 64% yield) as tan crystals.

Melting point: 191.5°–193.5° C. (decomp).

EXAMPLE 15

N-[7-[[(3,4-dimethyl-5-isoxazolyl)amino]sulfonyl]-1-naphthalenyl]acetamide

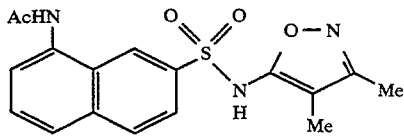

A. Sodium 8-acetylamino-2-naphthalenesulfonate

To a suspension of 8-amino-2-napthalene-sulfonic acid (10.0g, 44.8 mmol) in water (250 mL) was added sodium hydroxide (5N, 9 mL, 45 mmol). The resultant solution was concentrated in vacuo. A portion of this material (10 g, 40.8 mmol) was then suspended in acetic anhydride (100 mL) and was then heated at 95° C. for 6 hours, cooled and concentrated in vacuo to provide a solid. This solid was taken up in water (100 mL) and heated at 55° C. for 2 days and then at 85° C. for 2 hours. The solution was then concentrated in vacuo to yield compound A as a solid (12.0 g).

B. 8-Acetylamino-2-naphthalenesulfonyl chloride

Compound A (4.00 g, 13.9 mmol) was added in portions to chlorosulfonic acid (12 mL) held at 0° C. The mixture was brought to room temperature and stirred for 5 hours. The reaction was carefully added to crushed ice (150 g). The mixture was stirred until the ice had melted and then the precipitate was collected by filtration, washed with water (3×20 mL) and dried in vacuo to yield 2.91 g (74%) of compound B.

C. N-[7-[[(3,4-dimethyl-5-isoxazolyl)amino]sulfonyl]-1-naphthalenyl]acetamide

To a solution of 3,4-dimethyl-5-isoxazolamine (408 mg, 1.83 mmol) and 4-dimethylaminopyridine (68 mg) in pyridine (5 mL) was added compound B (800 mg, 2.80 mmol). The mixture was heated to 75° C. for 4 hours. The reaction mixture was cooled to room temperature, poured into water (30 mL) and brought to pH 1.5 with 6N hydrochloric acid. The sticky mixture was stirred for 17 hours. The resultant precipitate was collected by filtration, washed with water (3×10 mL) and dried in vacuo. Recrystallization of this material from ethanol/water yielded Example 15 (847 mg, 84% yield).

Melting point: 133.0°–134.0° C.

EXAMPLE 16

N-(3,4-Dimethyl-5-isoxazolyl)-5-methoxy-1-naphthalenesulfonamide

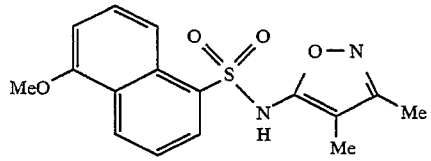

A. 5-Methoxy-1-naphthalenesulfonic acid, sodium salt

A solution of the sodium salt of 5-hydroxy-1-naphthalenesulfonic acid (10 g, 40.6 mmol), dimethylsulfate (3.7 mL, 40.6 mmol) and 4N sodium hydroxide (10.1 mL, 40.6 mmol) in 20 mL of 1:1 water:ethanol was refluxed overnight, cooled, acidified with concentrated hydrochloric acid and evaporated. The grey metallic solid was washed with ether to afford 12.4 g (greater than 100%) of impure compound A as a grey solid.

B. 5-Methoxy-1-naphthalenesulfonyl chloride

A mixture of the crude compound A (4.2 g, 16.1 mmol) and phosphorus pentachloride (6.73 g, 32.3 mmol) was heated at 70° C. with stirring for 2 hours, during which time the solids liquefied to a grey-green gum. Ice water was added to the mixture and the grey-green solid was filtered, washed with water, and taken up in dichloromethane, and the solution was dried (magnesium sulfate) and evaporated to afford compound B as a grey-green gum that crystallized on standing.

C. N-(3,4-Dimethyl-5-isoxazolyl)-5-methoxy-1-naphthalenesulfonamide

A solution of compound B (1.4 g, 5.5 mmol), 3,4-dimethyl-5-isoxazolamine (0.74 g, 6.59 mmol) and dimethylaminopyridine (0.17 g, 1.37 mmol) in 5 mL of pyridine was heated at 75° C. for 2 hours and poured onto ice. The solution was acidified with concentrated hydrochloric acid and the resulting brown solid was filtered, rinsed with water and dissolved in saturated sodium bicarbonate (150 mL). Celite ® was added, the suspension was filtered and the flitrate was acidified with concentrated hydrochloric acid. The resulting tan solid was filtered, rinsed with water and dried under vacuum to afford 1.10 g of tan solid. Chromatography on silica with 3% methanol/methylene chloride afforded 0.29 g of Example 16 (16%) as a tan solid.

Melting point: 72°–75° C. $^{13}$C NMR (CDCl$_3$) 6.38, 10.73, 55.75, 105.10, 107.62, 116.02, 123.37, 126.57, 129.10, 129.30, 129.42, 130.51, 133.82, 154.40, 155.94, 161.79 ppm.

EXAMPLE 17

N-(3,4-Dimethyl-5-isoxazolyl)-1-napthalenesulfonamide

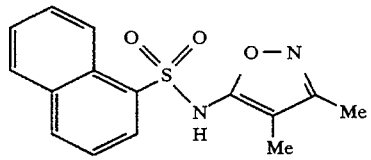

To a 0° C. solution of 3,4-dimethyl-5-isoxazolamine (1.19 g, 10.6 mmol) in pyridine (5 mL) was added 1-napthalenesulfonyl chloride (2.00 g, 8.82 mmol) in one portion. The reaction was allowed to come to room temperature. A precipitate soon formed. The reaction was stirred for 2 hours and was then added dropwise to water (50 mL). The pH was adjusted to 8 with 2N sodium hydroxide and the mixture was stirred for 30 minutes. A thick gum was present. The solution was decanted from the gum. The gum was rinsed with water and the combined decantates were brought to pH 2 with 6N hydrochloric acid and were stirred overnight, affording a clear, glassy solid. After decanting the solvent, the glassy solid was dried in vacuo. The gum from above was stirred with methanol (about 4 mL), causing a solid to form. The mixture was diluted with water (75 mL), brought to pH 2 with 6N hydrochloric acid and stirred overnight, depositing a solid that was collected, washed with water (2×20 mL) and similarly dried. This solid and the dried glassy solid were combined with 1N sodium hydroxide (20 mL). After stirring the mixture for 40 minutes, the precipitate was removed by filtration and the filtrate was brought to pH 2. The pale red precipitate was collected by filtration, rinsed with water (2×5 mL), and dried to yield a solid. Chromatography (flash, silica, 25 mm dia, 30% ethyl acetate/methylene chloride) yielded Example 17 as a white foam (700 mg, 26%).

Melting point: 54.0°–57.5° C. Analysis for $C_{15}H_{14}N_2O_3S \cdot 0.02\ H_2O$ Calc'd: C, 59.52; H, 4.67; N, 9.25; S, 10.59. Found: C, 59.64; H, 4.91; N, 9.13; S, 10.27.

EXAMPLE 18

5-[(1-Methylethyl)amino]-N-(3,4-dimethyl-5-isoxazolyl)-1-naphthalenesulfonamide

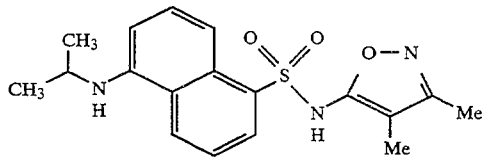

To a solution of Example 3 (0.150 g, 0.473 mmol) in 10 mL of methanol, was added acetone (0.035 g, 0.473 mmol). The resulting clear yellow solution was stirred for 45 minutes. Sodium cyanoborohydride (0.058 g, 0.95 mmol) and acetic acid (0.172 g, 2.85 mmol) were added and the mixture was stirred overnight at room temperature. The reaction mixture was concentrated in vacuo, taken up in 20 mL of water and extracted with ethyl acetate (3×30 mL). The combined organic layers were washed with brine (1×35 mL), dried (magnesium sulfate) and concentrated in vacuo to give 0.21 g of a yellow solid. This material was chromatographed (50 g Merck silica gel) using ethyl acetate:hexanes (1:1) as the eluant to give 0.101 g (60%) of Example 18 as a yellow solid.

Melting point: 156°–159° C.

EXAMPLE 19

N-[5-[[(3,4-Dimethyl-5-isoxazolyl)amino]sulfonyl]-1-naphthalenyl]-2-methylpropanamide

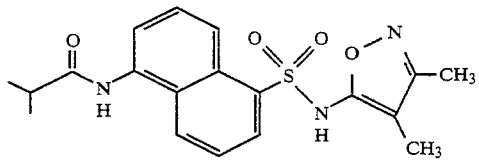

Isobutyryl chloride (0.144 mL, 1.38 mmol) was added dropwise to a solution of Example 3 (0.350 g, 1.10 mmol) in pyridine (1 mL) and acetone (7 mL). The mixture was stirred for 2.5 hours and the acetone was removed under vacuum to leave a thick brown residue, which was added dropwise to half-saturated sodium hydrogen carbonate (30 mL). The pH of the resulting mixture was adjusted to 8–8.5 with saturated sodium hydrogen carbonate. The crude product was precipitated by acidifying the solution to pH 1.5 with 6N hydrochloric acid, filtered and dried. Recrystallization from methanol/water afforded 51% of a solid.

Melting point: 177.1°–180.2° C. Analysis for $C_{19}H_{21}N_3O_4S$. Calc'd: C, 58.90; H, 5.46; N, 10.85; S, 8.27. Found: C, 58.97; H, 5.24; N, 10.83; S, 8.10.

EXAMPLE 20

5-Chloro-N-(3,4-dimethyl-5-isoxazolyl)-1-naphthalenesulfonamide

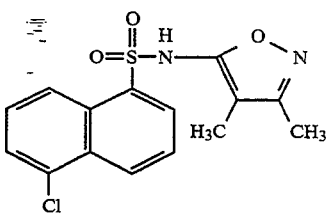

To a suspension of 5-chloronaphthalene sulfonylchloride (0.5 g, 1.9 mmol) in 10 mL of dry pyridine under argon, was added 5-amino-3,4-dimethylisoxazole (0.256 g, 2.28 mmol) and dimethylaminopyridine (50 mg, 10% w/w). The solution was stirred overnight and was heated at 60° C. for 6 hours. After cooling to room temperature, the mixture was poured into 30 mL of water, acidified with 6N hydrochloric acid to pH 2-3 and extracted with ethyl acetate (3×50 mL). The combined organic extracts were washed with brine, dried (magnesium sulfate) and concentrated under vacuum to give 0.61 g of brown gum. Flash chromatography (silica gel,) with 2:1 ethyl acetate:hexanes gave 0.27 g (81%) of Example 20 as a white solid.

Melting point 155°-158° C. Analysis for $C_{15}H_{13}ClN_2O_3S$ Calc'd: C, 53.49; H, 3.89; N, 8.32; S, 9.52; Cl, 10.53 Found: C, 53.92; H, 3.76; N, 8.18; S, 9.11; Cl, 10.37

EXAMPLE 21

N-(3,4-Dimethyl-5-isoxazolyl)-5-[(phenylmethyl)amino]-1-naphthlenesulfonamide

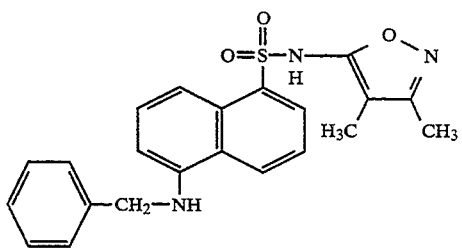

To a solution of Example 3 (0.26 g, 0.84 mmol) in 10 mL of methanol was added benzaldehyde (0.13 g, 1.25 mmol) and sodium cyanoborohydride (0.10 g, 1.67 mmol). The solution was stirred 15 minutes, acetic acid (0.29 mL, 5.00 mmol) was added and the solution was stirred overnight. Additional portions of benzaldehyde (0.026 g), sodium cyanoborohydride (0.021 g) and acetic acid (0.06 mL) were added and the mixture was stirred for 4 hours. The mixture was concentrated, suspended in 30 mL of water and extracted with 3×40 mL of ethyl acetate. The combined organic phases were washed with 50 mL of brine, dried (magnesium sulfate) and concentrated to a brown solid. Flash chromatography (silica gel) with ethyl acetate: hexanes (1:1) and a second chromatography with methylene chloride:methanol (96:4) gave 180 mg of yellow solid which upon trituration with ether:hexanes (30:70) afforded 150 mg (44%) of Example 21 as a yellow solid.

Melting point 140°-142° C. Analysis for $C_{22}H_{21}N_3O_3S$ Calc'd: C, 64.85; H, 5.19; N, 10.31; S, 7.87 Found: C, 64.82; H, 5.13; N, 10.12; S, 7.86

EXAMPLE 22

N-(3,4-Dimethyl-5-isoxazolyl)-5-hydroxy-1-naphthalenesulfonamide

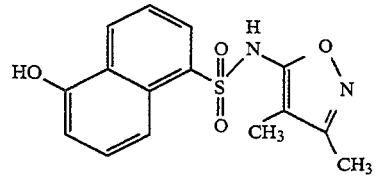

A. 5-(((4-methylphenyl)sulfonyl)oxy)-1-naphthalenesulfonic acid, sodium salt

A solution of the sodium salt of 5-hydroxy-1-naphthalenesulfonic acid (21.3 g, 86.5 mmol) and toluenesulfonyl chloride (16.5 g, 86.5 mmol) in a mixture of 20 mL water, 20 mL ethanol and 20 mL of 5N sodium hydroxide was heated at 100° C. for 3 hours and cooled. The tan solid was filtered, washed 3 times with water and dried overnight under vacuum at 50° C. to afford 16.0 g of Compound A. The combined filtrate and water washes deposited additional tan solid which was filtered, washed with water and dried under vacuum to afford an additional 5.9 g of Compound A (63% total).

B. 5-(((4-methylphenyl)sulfonyl)oxy)-1-naphthalenesulfonyl chloride

Compound B was prepared from compound A following the procedures of part B of Example 16 (100% yield of a grey-green gum which crystallized on standing).

C. N-(3,4-dimethyl-5-isoxazolyl)-5-(((4-methylphenyl)sulfonyl)oxy)-1-naphthalenesulfonamide Compound C was prepared from compound B following the procedures of part C of Example 16. After the reaction was poured onto iced dilute hydrochloric acid, the resulting tan solid was filtered, rinsed with water and dissolved in ethyl acetate. The solution was dried (magnesium sulfate) and evaporated to afford a tan foamy solid which was flash chromatographed on silica (75% ethyl acetate/hexanes) to provide Compound C as a light yellow foamy solid.

D. N-(3,4-Dimethyl-5-isoxazolyl)-5-hydroxy-1-naphthalenesulfonamide

A solution of Compound C (0.36 g, 0.78 mmol) and 4N sodium hydroxide (0.98 mL, 3.92 mmol) in 5 mL of methanol was heated at 65° C. for 21.5 hours, cooled and acidified with 10% hydrochloric acid. The methanol was evaporated and the residue was extracted twice with 10% isopropanol/methylene chloride. The combined organic phases were dried (magnesium sulfate) and evaporated to afford 0.39 g of red-brown gum with some crystalline material. Recrystallization from aqueous ethanol afforded 0.149 g of pink solid. This material was subjected to preparative TLC on silica with ethyl acetate and the product band was extracted with 10% isopropanol/methylene chloride. Evaporation of the organic solution afforded 0.122 g (49%) of Example 22 as a light pink solid.

Melting point 201°-203° C. Analysis for $C_{15}H_{14}N_2O_4S$ Calc'd: C, 56.59; H, 4.43; N, 8.80; S, 10.07. Found: C, 56.44; H, 4.33; N, 8.60; S, 9.80.

EXAMPLE 23

7-(Dimethylamino)-N-(3,4-dimethyl-5-isoxazolyl)-1-naphthalenesulfonamide

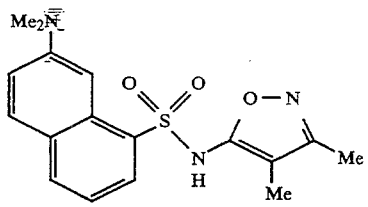

A solution of Example 48 (100 mg, 0.315 mmol) and sodium cyanoborohydride (139 mg, 2.21 mmol) in tetrahydrofuran (2 mL) was added dropwise to a 0° C. solution of formaldehyde (37%, 13.3M, 0.14 mL, 1.9 mmol) and 3M sulfuric acid (0.1 mL) in tetrahydrofuran (2 mL). The reaction was stirred at 0° C. for 1.5 hours and was then made basic with 2N sodium hydroxide (2 mL). The tetrahydrofuran was removed under vacuum and the solution was brought to pH 3.5 with 1N hydrochloric acid. The mixture was stirred for 1 hour and the precipitate was collected by filtration, washed with water (2×2 mL), dried, chromatographed (silica, 2% methanol/methylene chloride) and recrystallized from ethanol/water to provide Example 23 (45%).

Melting point 222°-223° C. Analysis for $C_{17}H_{19}N_3O_3S$-0.07 $H_2O$. Calc'd: C, 58.90; H, 5.57; N, 12.12; S, 9.25. Found: C, 58.54; H, 5.42; N, 12.10; S, 9.68.

EXAMPLE 24

N-(3,4-Dimethyl-5-isoxazolyl)-5-[methyl(1-methylethyl)amino]-1-naphthalenesulfonamide

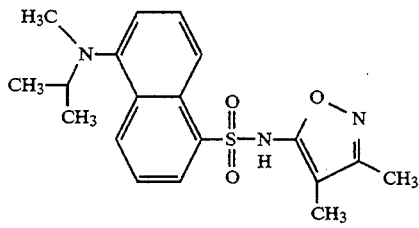

To a solution of Example 18 (0.25 g, 0.70 mmol) in 5 mL of methanol, 37% aqueous formaldehyde (170 mL, 2.08 mmol) was added and the solution was stirred for 5 minutes. Glacial acetic acid (0.2 mL) was added and then sodium cyanoborohydride (0.13 g, 2.08 mmol) was added in one portion and the mixture was stirred overnight. The solution was concentrated and diluted with 25 mL of water and the yellow solid thus obtained was filtered and dried. Recrystallization from hexanes/ethyl acetate provided 0.21 g (81%) of Example 24 in two crops.

Melting point 132°-133° C. Analysis for $C_{19}H_{23}N_3O_3S$-1.19 $H_2O$ Calc'd: C, 57.78; H, 6.48; N, 10.64; S, 8.12. Found: C, 57.74; H, 6.04; N, 10.68; S, 8.34.

EXAMPLE 25

2-[[5-[[(3,4-Dimethyl-5-isoxazolyl)amino]sulfonyl]-1-naphthalenyl]amino]propanoic acid, ethyl ester

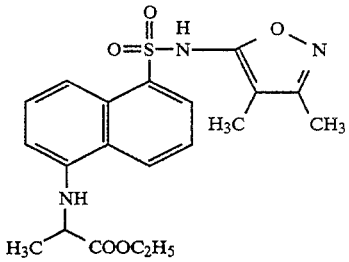

Example 25 was prepared as a yellow solid from Example 3 and ethyl pyruvate as described for Example 21.

Melting point 62°-65° C. Analysis for $C_{20}H_{23}N_3O_5S$-0.12 $H_2O$ Calc'd: C, 58.03; H, 5.90; N, 9.71; S, 7.41. Found: C, 58.03; H, 5.78; N, 9.32; S, 7.3.

EXAMPLE 26

N-(3,4-Dimethyl-5-isoxazolyl)-5-(2-oxo-1-pyrrolidinyl)-1-naphthalenesulfonamide

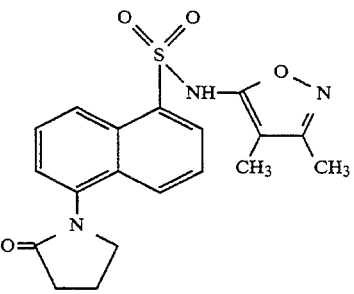

A. N-(3,4-Dimethyl-5-isoxazolyl)-5-[1-(4-bromo-1-oxobutyl)amino]-1-naphthalenesulfonamide To a solution of Example 3 (300 mg, 0.95 mmol) and pyridine (0.11 mL, 1.41 mmol) in dichloromethane (15 mL) was added 4-bromobutyryl chloride (0.12 mL, 1.04 mmol). The mixture was stirred at room temperature for 90 minutes and extracted with 10% aqueous sodium bicarbonate (three times). The combined aqueous extracts were acidified to pH 3 with 6N hydrochloric acid and extracted with dichloromethane (three times). The combined organic phases were washed with brine, dried (magnesium sulfate) and evaporated to afford 263 g (47%) of compound A as a tan solid.

B. N-(3,4-Dimethyl-5-isoxazolyl)-5-(2-oxo-1-pyrrolidinyl)-1-naphthalenesulfonamide To a slurry of cesium carbonate (290 mg, 0.90 mmol) in dry dimethylformamide (5 mL) at 60° C. was added a solution of compound A (210 mg, 0.45 mmol) in 5 mL of dry dimethylformamide dropwise over 30 minutes. The mixture was stirred for 90 minutes, evaporated and the residue was partitioned between ethyl acetate and water. The aqueous layer was extracted with ethyl acetate (twice), acidified to pH 3 with 6N hydrochloric acid and extracted with dichloromethane (three times). The combined dichloromethane phases were washed with brine, dried (magnesium sulfate) and evaporated. The residue was crystallized from ethyl acetate/hexanes and the crystalline solid was triturated with hexanes to afford 124 mg (73%) of Example 26 as a tan solid.

Melting point: 183°–187° C. Analysis for $C_{19}H_{19}N_3SO_4$: 0.79 $H_2O$ Calc'd: C, 57.11; H, 5.19; N, 10.51; S, 8.02. Found: C, 57.25; H, 5.03; N, 10.37; S, 8.36.

EXAMPLE 27

N-(3,4-Dimethyl-5-isoxazolyl)-5-(2-oxo-1-piperidinyl)-1-naphthalenesulfonamide

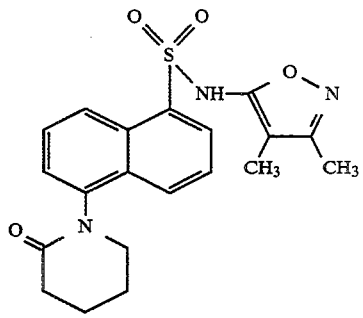

A. N-(3,4-Dimethyl-5-isoxazolyl)-5-[1-(5-bromo-1-oxopentyl)amino]-1-naphthalenesulfonamide Compound A was prepared as a tan solid from Example 3 and 5-bromovalerylchloride as described for compound A of Example 26.

B. N-(3,4-Dimethyl-5-1-isoxazolyl)-5-(2-oxo-1-piperidinyl)-1-naphthalenesulfonamide Example 27 was prepared from Compound A as a brown solid as described for Example 26.

Melting point: 203°–208° C. Analysis for $C_{20}H_{21}N_3SO_4$: 0.06 $H_2O$ Calc'd: C, 59.97; H, 5.31; N, 10.49; S, 8.00. Found: C, 59.66; H, 5.45; N, 10.80; S, 8.06.

EXAMPLE 28

N-(3,4-Dimethyl-5-isoxazolyl)-5-[[(phenylamino)thioxomethyl]amino]-1-naphthalenesulfonamide

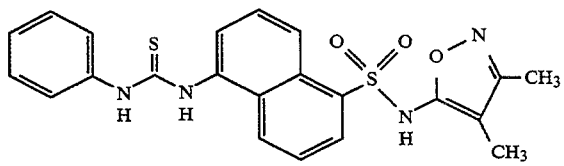

Phenylisothiocyanate (0.62 mL, 5.2 mmol) was added dropwise to a solution of Example 3 (1.26 g, 3.97 mmol), triethylamine (1.3 mL, 9.3 mmol), and dimethylaminopyridine (0.100 g, 0.819 mmol) in acetone (45 mL). The mixture was refluxed at 65° C. After 48 hours another 0.3 equivalents (0.1 mL) of phenylisothiocyanate was added, and the reaction was refluxed for an additional 120 hours. The acetone was evaporated, and half-saturated sodium hydrogen carbonate (75 mL) was added to the brown residue. The mixture was allowed to stir overnight and was filtered to collect a brown solid. The residual black gum left in the flask was stirred with another 50 mL of half-saturated sodium hydrogen carbonate for 1 hour and filtered. The combined filter cakes were dried, chromatographed (silica, 2% followed by 10% methanol/methylene chloride) and rechromatographed on an HP-20 column eluting with 25%, 30% then 35% methanol/water solutions containing 0.2% ammonium hydroxide to yield Example 28 as a pale yellow solid (87 mg, 6%).

Melting point 137°–138° C. Analysis for $C_{22}H_{20}N_4O_3S_2$-1.90 $H_2O$-0.75 $NH_3$. Calc'd: C, 52.90; H, 5.26; N, 13.32; S, 12.84. Found: C, 52.67; H, 4.92; N, 13.22; S, 13.25.

EXAMPLE 29

N-(3,4-Dimethyl-5-isoxazolyl)-5-(1-pyrrolidinyl)-1-naphthalenesulfonamide

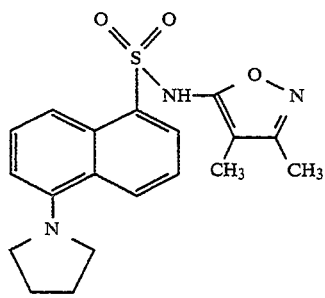

A. N-(3,4-Dimethyl-5-isoxazolyl)-5-(4-chlorobutylamino)-1-naphthalenesulfonamide A solution of 2-(3-chloropropyl)-1,3-dioxolane (1.25 mL, 9.45 mmol) in 5% aqueous hydrochloric acid (3 mL) and dioxane (3 mL) was stirred overnight. A slurry of Example 3 (3.0 g, 9.45 mmol) in glacial acetic acid (50 mL) was added and the mixture was stirred at 0° C. for 1 hour. Sodium cyanoborohydride (4.66 g, 64.6 mmol) was added in portions over 3 hours and the mixture was stirred overnight at room temperature and evaporated. The residue was partitioned between dichloromethane and water and the aqueous layer was acidified to pH 3 with 6N hydrochloric acid and extracted with dichloromethane (three times). The combined organic phases were washed with brine, dried (magnesium sulfate) and evaporated to afford 2.13 g (55.4%) of Compound A as a yellow solid.

B. N-(3,4-Dimethyl-5-isoxazolyl)-5-(1-pyrrolidinyl)-1-naphthalenesulfonamide

A solution of Compound A (2.13 g, 5.23 mmol) and N-methyl-morpholine (4 mL) in dimethylformamide (25 mL) was heated to 75° C. for 4 hours. The solvent was removed under vacuum and the residue was dissolved in water. The aqueous solution was acidified to pH 3 with 6N hydrochloric acid, extracted with ethyl acetate (three times) and the combined organic phases were washed with brine, dried (magnesium sulfate) and evaporated. The residue was chromatographed on silica with ethyl acetate:hexanes (1:1) to afford 320 mg of a yellow semisolid, which was recrystallized from aqueous ethanol to afford 159 mg (7%) of Example 29 as a green solid.

Melting point: 172°–173° C. Analysis for $C_{19}H_{21}N_3SO_3$:0.51 $H_2O$ Calc'd: C, 59.96; H, 5.83; N, 11.04; S, 8.42. Found: C, 59.98; H, 5.53; N, 11.02; S, 8.34.

EXAMPLE 30

5-[[(3,4-Dimethyl-5-isoxazolyl)amino]sulfonyl]-1-naphthalenecarboxylic acid

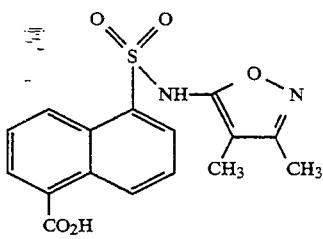

A solution of Example 32 (6 g, 16.7 mmol) in 4N sodium hydroxide (20 mL) and methanol (100 mL) was stirred at room temperature for 2.5 hours. The organic solvent was evaporated and the aqueous residue was acidified to pH 3 with 6N hydrochloric acid. The resulting tan solid was collected by filtration, rinsed with water, and dried to afford 4.2 g of Example 30 (72%) as a tan solid. The filtrate was extracted with dichloromethane, the organic phase was washed with saturated sodium chloride, dried (magnesium sulfate), filtered and evaporated to afford an additional 1.0 g of Example 30.

Melting point 202°–204° C. Analysis for $C_{16}H_{14}N_2SO_5 \cdot 0.32\ H_2O$ Calc'd: C, 54.58; H, 4.19; N, 7.96; S, 9.11. Found: C, 54.55; H, 4.18; N, 7.99; S, 9.05.

EXAMPLE 31

5-[[[5-(Dimethylamino)-1-naphthalenyl]sulfonyl]amino]-3-methyl-4-1-isoxazolecarboxylic acid, ethyl ester

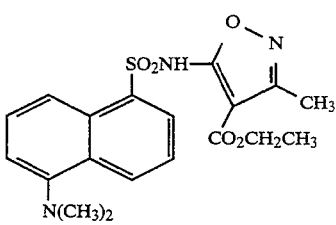

A. Ethylbromopropiolate

To a solution of ethylpropiolate (15.2 mL, 150 mmol) in acetone (250 mL) was added silver nitrate (2.51 g, 15 mmol) followed by N-bromosuccinimide (1.34 mL, 9.60 mmol). The solution was stirred for 1 hour and the volatiles were removed from the grey heterogeneous solution under vacuum and collected in a trap at $-78°$ C. The semi-solid residue was partitioned between ether and water, the ether layer was washed with brine, dried (magnesium sulfate) and evaporated under low pressure to remove ether. The oily residue was combined with the trapped volatiles solution and the resulting solution was distilled, first at atmospheric pressure to remove most of the acetone and then at 7 mm, with Compound A distilling at 52°–58° C. as a clear oil which turned light brown on standing (22.1 g, 83%).

B. 3-methyl-5-bromo-4-ethoxycarbonylisoxazole

To a solution of Compound A (15.4 g, 87 mmol) and acetaldoximine (7.94 mL, 130 mmol) in methylene chloride (50 mL) was added clorox (277 mL, about 208 mmol) dropwise over 2.5 hours. The blue-green solution was stirred 30 minutes, partitioned, the aqueous phase was washed with methylene chloride and the combined organic phases were dried (magnesium sulfate) and evaporated to afford 22.2 g of orange oil. Flash chromatography on silica with 10% ether/hexanes afforded 7.44 g (36%) of a 2:1 mixture of Compound B and 3-methyl-4-bromo-5-ethoxycarbonylisoxazole as a clear oil.

C. 5-[[[5-(Dimethylamino)-1-naphthalenyl]sulfonyl]amino]-3-methyl-4-isoxazolecarboxylic acid, ethyl ester A solution of compound B (2.03 g of a 2:1 mixture of regioisomers, 8.67 mmol), dansylamide (2.17 g, 8.67 mmol) and cesium carbonate (5.64 g, 17.3 mmol) was heated at 77° C. in dimethylformamide (10 mL) for 3 hours and the bulk of the solvent was removed under vacuum with heating. The residue was partitioned between methylene chloride and 5% aqueous potassium hydrogen sulfate, the aqueous phase was washed with methylene chloride and the combined organic phases were dried (magnesium sulfate) and evaporated to afford 7.8 g of brown oil. The oil was dissolved in 200 mL of ether and filtered of a small amount of brown solid. The filtrate was evaporated and warmed under high vacuum to remove additional dimethylformamide, affording 4.26 g of light brown oil. The oil was passed through a pad of silica with ethyl acetate to afford 3.30 g of yellow solid which was dissolved in ether and filtered. The filtrate was evaporated and subjected to flash chromatography on silica with ethyl acetate to provide 0.24 g of clean Example 31 as a light yellow foam and 2.2 g of impure Example 31 as a yellow foam. The impure material was dissolved in ether and chilled to afford 0.54 g (15%) of Example 31 as yellow cubes which became an amorphous solid on gentle warming under vacuum.

Melting point 146°–148° C. Analysis for $C_{19}H_{21}N_3O_5S$ Calc'd: C, 56.56; H, 5.25; N, 10.42; S, 7.95. Found: C, 56.63; H, 5.31; N, 10.22; S, 7.82.

EXAMPLE 32

5-[[(3,4-Dimethyl-5-isoxazolyl)amino]sulfonyl]-1-naphthalenecarboxylic acid, methyl ester

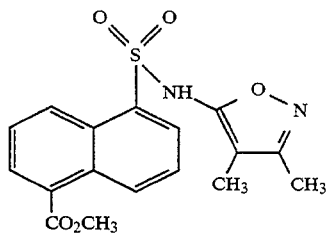

A solution of 5-chlorosulfonyl-1-naphthalenecarboxylic acid, methyl ester (15 g, 52.7 mmol), dimethylaminopyridine (500 mg, 4.09 mmol), and 5-amino-3,4-dimethylisoxazole (6.02 g, 55.3 mmol) in pyridine (150 mL) was heated at 70° C. overnight. The mixture was concentrated to half volume, poured into iced 10% aqueous hydrochloric acid and extracted with ethyl acetate (three times). The combined organic phases were extracted with 10% aqueous sodium hydrogen carbonate. The aqueous solution was acidified to pH 3 with 6N hydrochloric acid and extracted with ethyl acetate (three times). The combined organic phases were washed with saturated sodium chloride, dried (magnesium sulfate), filtered and evaporated to afford 11.1 g (59%) of Example 32 as a tan solid.

EXAMPLE 33

5-(Dimethylamino)-N-(3-methyl-5-isoxazolyl)-1-naphthalenesulfonamide

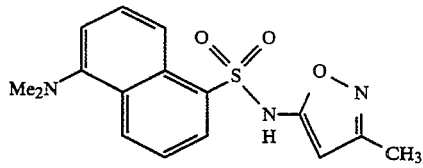

To a solution of Example 31 (325 mg, 0.80 mmol) in 95% ethanol (9 mL) was added 1N sodium hydroxide (4 mL, 4 mmol). The solution was heated at reflux for 3 hours, the ethanol was evaporated and aqueous 5% potassium hydrogen sulfate was added to the residue. The mixture was extracted twice with 10% isopropanol/methylene chloride and the combined organic phases were dried (magnesium sulfate) and evaporated to afford 0.37 g of green foamy solid. After combination with approximately 70 mg of product from a previous reaction, the solid was recrystallized from ethyl acetate/hexanes to afford 111 mg (35%) of Example 33 as green crystals.

Melting point 183°-187° C. Analysis for $C_{16}H_{17}N_3O_3S \cdot 0.53\ H_2O$ Calc'd: C, 56.36; H, 5.34; N, 12.32; S, 9.40. Found: C, 55.96; H, 4.91; N, 12.09; S, 9.50.

EXAMPLE 34

5-[(Dimethylamino)methyl]-N-(3,4-dimethyl-5-isoxazolyl)-1-naphthalenesulfonamide, trifluoroacetate (1:1) salt

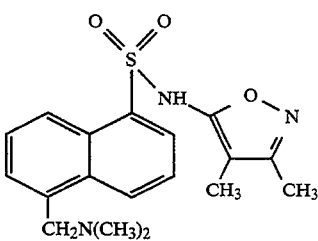

A. 5-[Hydroxymethyl]-N-(3,4-dimethyl-5-isoxazolyl)-1-naphthalenesulfonamide

To a solution of Example 30 (1.5 g, 4.32 mmol) in dry tetrahydrofuran (60 mL) at 0° C. was added a 1M solution of borane:tetrahydrofuran (15 mL, 15.0 mmol) dropwise over 1 hour. The mixture was stirred at 0° C. for 1 hour and at room temperature for 4 hours and was poured into 150 mL of 3N hydrochloric acid. The solution was extracted with ethyl acetate (three times) and the combined organic phases were washed with brine, dried (magnesium sulfate) and evaporated. The residue was dissolved in ether and the solution was washed with water and brine, dried (magnesium sulfate) and evaporated to afford 1.5 g (100%) of Compound A as a tan solid.

B. 5-[[(3,4-Dimethyl-5-isoxazolyl)amino]sulfonyl]-1-naphthaldehyde

To mixture of compound A (1.5 g, 4.51 mmol) in dichloromethane (150 mL) was added pyridinium chlorochromate (1.33 g, 6.9 mmol). The mixture was stirred at room temperature for 30 minutes, applied to a pad of fluorisil and eluted with 600 mL of 10% methanol/dichloromethane. The eluent was concentrated to 200 mL, washed with brine, dried (magnesium sulfate) and evaporated to afford 1.22 g (82%) of compound B as a brown solid.

C. 5-[(Dimethylamino)methyl]-N-(3,4-dimethyl-5-isoxazolyl)-1-naphthalenesulfonamide, trifluoroacetate (1:1) salt To a solution of compound B (800 mg, 2.42 mmol), acetic acid (0.138 mL, 2.42 mmol), and dimethylamine (1.82M in dry tetrahydrofuran, 1.73 mL, 3.15 mmol) in dry tetrahydrofuran (50 mL) was added sodium triacetoxyborohydride (710 mg, 3.38 mmol). The mixture was stirred at room temperature for 48 hours, additional acetic acid (0.069 mL, 1.21 mmol), dimethylamine (0.86 mL, 1.58 mmol) and sodium triacetoxyborohydride (355 mg, 1.69 mmol) were added and the mixture was stirred for 24 hours and evaporated. The residue was partitioned between dichloromethane and 4N aqueous hydrochloric acid and the aqueous layer was lyophilized to afford 245 mg of a white lyophilizate. The lyophilizate was dissolved in 20 mL of 80% aqueous acetonitrile containing 0.1% trifluoroacetic acid and the solution was subjected to gradient preparative HPLC (85% to 40% aqueous acetonitrile containing 0.1% trifluoroacetic acid). Fractions containing clean product were pooled and lyophilized and the residue was triturated with ether to afford 144 mg (17%) of Example 34 as a tan solid.

Analysis for $C_{18}H_{21}N_3O_3S \cdot 1.66\ H_2O \cdot 1.2\ CF_3CO_2H$ Calc'd: C, 46.56; H, 4.84; N, 7.98; S, 6.09. Found: C, 46.56; H, 4.45; N, 7.85; S, 5.92. $^{13}C$ NMR: ($CDCl_3/CD_3OD$) 4.93, 9.17, 42.18, 57.2, 125.75, 127.00, 127.32, 129.25, 129.4, 130.43, 132.02, 133.0, 136.1, 163.15 ppm.

EXAMPLE 35

N-(3,4-Dimethyl-5-isoxazolyl)-5-(1-hydroxy-1-methylethyl)-1-naphthalenesulfonamide

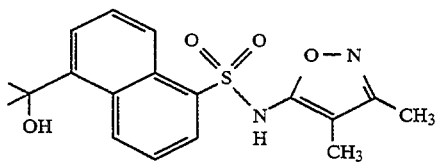

To a solution of Example 32 (0.99 g, 2.75 mmol) in dry tetrahydrofuran (50 mL) was added methyl magnesium bromide (4.58 mL of a 3M solution in ether, 13.7 mmol). The solution was heated at reflux for 75 minutes, quenched with 5% aqueous potassium hydrogen sulfate and extracted with ethyl acetate and the organic phase was washed with brine, dried (magnesium sulfate) and evaporated. The residue was combined with the product of a previous reaction (0.55 mmol scale) to afford 1.26 g of off-white foamy solid. Chromatography on silica (flash; 75% ethyl acetate/hexanes) afforded 0.28 g (24%) of Example 35 as a white foamy solid (melting point 97°-101° C.) as well as 0.40 g of slightly less pure material.

Analysis for $C_{18}H_{20}N_2O_4S$ Calc'd: C, 59.98; H, 5.59; N, 7.77; S, 8.90. Found: C, 59.74; H, 5.81; N, 7.76; S, 8.55.

---

Melting point 173°-178° C. Analysis for $C_{17}H_{16}N_2SO_5 \cdot 0.18\ H_2O$ Calc'd: C, 56.16; H, 4.53; N, 7.71; S, 8.82. Found: C, 55.85; H, 4.43; N, 8.02; S, 8.41.

EXAMPLE 36

N-(3,4-Dimethyl-5-isoxazolyl)-5-(1-methylethenyl)-1-naphthalenesulfonamide

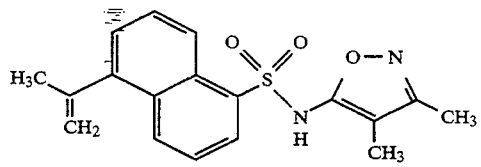

A solution of Example 35 (0.40 g, 1.11 mmol) and trifluoroacetic acid (0.17 mL, 2.21 mmol) in methylene chloride (5 mL) was heated at reflux for 5 hours. Additional methylene chloride was added and the solution was washed with water, dried (magnesium sulfate) and evaporated to afford 0.31 g of an off-white foamy solid. Chromatography on silica (flash; 60% ethyl acetate/hexanes) afforded 0.27 g (71%) of Example 36 as an off-white foamy solid.

Melting point 65°-70° C. Analysis for $C_{18}H_{18}N_2O_3S$ Calc'd: C, 63.14; H, 5.30; N, 8.18; S, 9.36. Found: C, 62.97; H, 5.45; N, 8.16; S, 9.03.

EXAMPLE 37

N-(3,4-Dimethyl-5-isoxazolyl)-5-(1-piperidinyl)-1-naphthalenesulfonamide, trifluoroacetate (2:1) salt

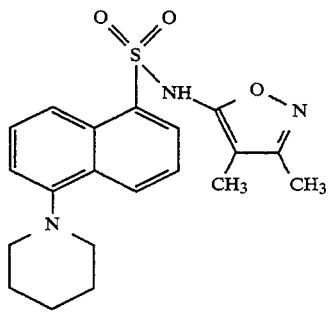

To a mixture of Example 3 (1.5 g, 4.71 mmol) in glacial acetic acid (40 mL) and dioxane (20 mL) at 0° C. was added a 50% solution of glutaric dialdehyde (0.85 g, 4.71 mmol). The mixture was stirred at 0° C. for 1 hour, sodium cyanoborohydride (1.5 g, 23.9 mmol) was added in portions over 1 hour and the mixture was stirred overnight and evaporated. The residue was partitioned between water and ethyl acetate and the aqueous layer was acidified to pH 3 with 6N hydrochloric acid and extracted with ethyl acetate (three times). The combined organic phases were washed with brine, dried (magnesium sulfate) and evaporated. The residue was chromatographed on silica with ethyl acetate:hexanes (1:1). Fractions containing product were combined and evaporated. The residue was dissolved in 80% aqueous acetonitrile containing 0.1% trifluoroacetic acid and subjected to gradient preparative HPLC (70% to 45% aqueous acetonitrile containing 0.1% trifluoroacetic acid). Fractions containing clean product were pooled and lyophilized from water to afford 48 mg (3%) of Example 37 as fluffy brown lyophilizate.

Melting point 89°-93° C. Analysis for $C_{20}H_{23}N_3O_3S$-1.26 $H_2O$-0.5 $CF_3CO_2H$ Calc'd: C, 54.22; H, 5.63; N, 9.00; S, 6.89. Found: C, 54.22; H, 5.27; N, 8.71; S, 6.87.

EXAMPLE 38

N-(3,4-Dimethyl-5-isoxazolyl)-5-(methylamino)-1-naphthalenesulfonamide

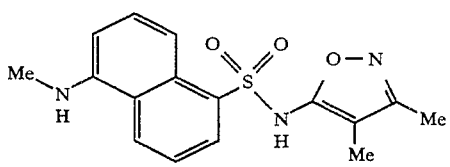

A. N-(3,4-Dimethyl-5-isoxazolyl)-N-((2-(trimethylsilyl)ethoxy)methyl)-5-amino-1-naphthalenesulfonamide Triethylamine (0.048 mL, 0.35 mmol) was added to a stirred suspension of Example 3 (100 mg, 0.32 mmol) in methylene chloride (3 mL). The homogeneous mixture was cooled to 0° C., during which time a precipitate formed. Trimethylsilylethoxymethyl chloride (0.061 mL, 0.35 mmol) was added dropwise and after 1 hour at 0° C., an additional 0.5 equivalents each of triethylamine and trimethylsilylethoxymethyl chloride were added sequentially. After an additional 1 hour, the reaction was loaded onto a silica column which was eluted with 25% and then 30% ethyl acetate/hexanes to provided compound A as an oil (78.1 mg, 55%).

B. N-(3,4-Dimethyl-5-isoxazolyl)-N-((2-(trimethylsilyl)ethoxy)methyl)-5-(methylamino)-1-naphthalenesulfonamide A slurry of 10% palladium on charcoal (250 mg) in methanol (1 mL) was added to a solution of compound A (528 mg, 1.18 mmol), formaldehyde (13M, 37%, 0.18 mL, 2.4 mmol), and acetic acid (0.67 mL, 1.2 mmol) in methanol (10 mL) under argon. The argon was replaced by hydrogen by 4 pump/purge cycles. The reaction was stirred at room temperature for 2.5 hours, the hydrogen was replaced with argon and the mixture was filtered through Celite ® AFA and concentrated under vacuum. Flash chromatography (silica, 35% ethyl acetate/hexanes) provided 340 mg (62%) of compound B as an oil.

C. N-(3,4-Dimethyl-5-isoxazolyl)-5-(methylamino)-1-naphthalenesulfonamide

To a 0° C. solution of compound B (224 mg, 0.48 mmol) in methylene chloride (2 mL) was added trifluoroacetic acid (4 mL). The reaction was stirred for 2.5 hours and was concentrated under vacuum. Flash chromatography (silica, 5% methanol/methylene chloride) and a second flash chromatography (silica, 60% ethyl acetate/hexanes) provided an oil. This material was dissolved in 5% sodium hydrogen carbonate (10 mL), the solution was filtered through Celite ®°AFA and the flitrate was brought to pH 4 with 6N hydrochloric acid. The greenish-yellow solid was collected by filtration, washed with water (2×5 mL) and dried to provide 147 mg (91%) of Example 38.

Melting point 92°-105° C. Analysis for $C_{16}H_{17}N_3O_3S$-0.65 $H_2O$ Calc'd: C, 55.86; H, 5.39; N, 12.22; S, 9.32. Found: C, 56.01; H, 5.38; N, 12.25; S, 9.34.

EXAMPLE 39

N-(3,4-Dimethyl-5-isoxazolyl)-5-(ethylamino)-1-naphthalenesulfonamide

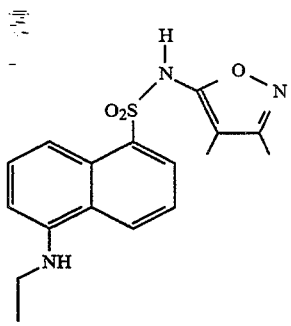

Example 2 (0.244 g, 0.62 mmol) was added to a solution of borane (1.0M in tetrahydrofuran, 1.9 mL, 1.9 mmol) in tetrahydrofuran (13 mL) stirring at 0° C. After stirring at 0° C. for 15 minutes, at ambient temperature for 1.25 hours, and at reflux for 2 hours, the reaction mixture was evaporated under vacuum. Water was slowly added to the residue and the mixture was acidified to pH 4.5 with 1N hydrochloric acid and extracted with methylene chloride (2×, 75 mL). The combined organic phases were dried (magnesium sulfate) and evaporated to afford 0.22 g of crude product. Flash chromatography (silica, 15 mm dia., 20% ethyl acetate/methylene chloride) afforded 0.12 g (58%) of Example 39.

Melting point 75.0°–85.0° C., decomposed. Analysis for $C_{17}H_{19}N_3O_3S$-0.25 $C_4H_8O_2$. Calc'd: C, 58.84; H, 5.76; N, 11.44. Found: C, 59.01; H, 5.82; N, 11.29.

EXAMPLE 40

N-(3-Methyl-4-phenylmethyl-5-isoxazolyl)-5-[dimethylamino]-1-naphthalenesulfonamlde

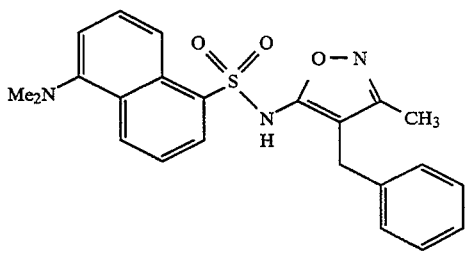

Prepared in 38% yield as a yellow foamy solid from dansyl chloride and 3-methyl-4-phenylmethyl-5-isoxazolamine as described for Example 20. The reaction was heated at 85° C. for 75 minutes. Flash chromatography was performed on silica with 25%, then 40%, then 60% ethyl acetate/hexanes.

Melting point 59°–65° C. Analysis for $C_{23}H_{23}N_3O_3S$-0.11 $H_2O$. Calc'd: C, 65.23; H, 5.53; N, 9.92; S, 7.57. Found: C, 65.23; H, 5.70; N, 9.72; S, 7.20.

EXAMPLE 41

N-(3-Methyl-4-phenyl-5-isoxazolyl)-5-(dimethylamino)-1-naphthalenesulfonamide

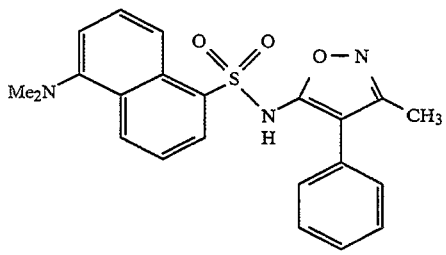

Prepared in 10% yield as a yellow foamy solid from dansyl chloride and a mixture of 3-methyl-4-phenyl-5-isoxazolamine and 5-methyl-4-phenyl-3-isoxazolamine as described for Example 20. The reaction was heated at 85° C. for 75 minutes. Flash chromatography was performed on silica with 50%, then 100% ethyl acetate/hexanes.

Melting point 78°–88° C. Analysis for $C_{22}H_{21}N_3O_3S$-0.37 $H_2O$. Calc'd: C, 63.81; H, 5.29; N, 10.15; S, 7.74. Found: C, 64.24; H, 5.39; N, 10.22; S, 7.34.

EXAMPLE 42

N-(3-Ethyl-4-methyl-5-isoxazolyl)-5-(dimethylamino)-1-naphthalenesulfonamide

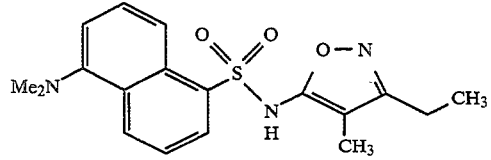

Example 42 was prepared in 20% yield as a yellow solid from dansyl chloride and 3-ethyl-4-methyl-5-isoxazolamine as described for Example 20. The reaction was heated at 75° C. for 3.5 hours. Flash chromatography was performed on silica with 40% ethyl acetate/hexanes. An analytical sample was prepared by dissolution in aqueous sodium hydrogen carbonate, filtration through Celite ®, acidification of the flitrate with solid potassium hydrogen sulfate and filtration and drying of the resulting yellow solid.

Melting point 51°–68° C. Analysis for $C_{18}H_{21}N_3O_3S$-0.52 $H_2O$. Calc'd: C, 58.62; H, 6.02; N, 11.39; S, 8.69. Found: C, 58.62; H, 5.73; N, 11.69; S, 8.68.

EXAMPLE 43

5-(Dibutylamino)-N-(3,4-dimethyl-5-isoxazolyl)-1-naphthalenesulfonamide, monosodium salt

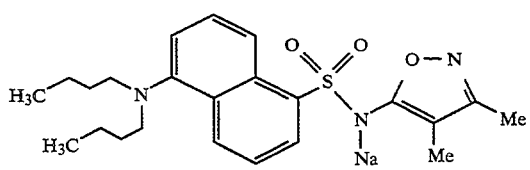

A solution of 5-dibutylamino-1-naphthalenesulfonyl chloride (906 mg, 2.56 mmol), 3,4-dimethyl-5-isoxazolamine (373 mg, 3.33 mmol) and 4-dimethylaminopyridine (63 mg, 0.51 mmol) in dry pyridine (5 mL) was heated at 70° C. for 3 hours. The reaction was cooled to room temperature and was poured into 50 mL of water. The mixture was brought to pH 4.5 with 6N hydrochloric acid, the water was decanted from the resulting gum and ether (100 mL) was added to the residue. The remaining precipitate was removed by filtration and combined with material from a previous 0.565-mmol scale reaction and the whole was chromatographed (flash, silica, 30% ethyl acetate/hexanes) to provide 618 mg of a yellow-green glass.

This material was suspended in half-saturated sodium hydrogen carbonate (20 mL), the solution was warmed to aid dissolution, and 1N sodium hydroxide was added to bring the pH to 10. Methanol (1 mL) was added to effect complete solution. The solution was loaded onto a methanol-activated, water-equilibrated Sep-Pak Cartridge (Waters, 10 g of tC18 packing). The column was washed with water (50 mL) and 10% methanol/water (20 mL). The product was eluted with methanol (30 mL). This eluate was concentrated under vacuum and the glassy residue was triturated with ether (10 mL) to provide, after filtration and drying, 524 mg (45%) of the title compound:

Melting point 130.0°–135.0° C. Analysis for $C_{23}H_{30}N_3O_3SNa\cdot0.63\ H_2O$. Calc'd: C, 59.68; H, 6.81; N, 9.08. Found: C, 59.61; H, 6.74; N, 9.00.

EXAMPLE 44

4-[1-[[(3,4-Dimethyl-5-isoxazolyl)amino]sulfonyl]naphthalen-5-yl]amino]butanoic acid

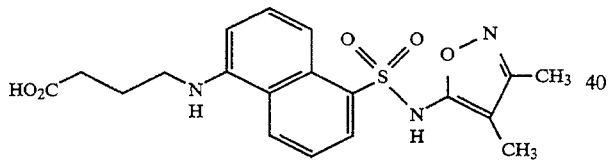

A solution of Example 26 (200 mg, 0.52 mmol) in methanol (5 mL) and aqueous 4N sodium hydroxide (15 mL) was heated at 70° C. for 52 hours. The solution was cooled to room temperature, acidified to pH 3 with 6N aqueous hydrochloric acid and the resulting yellow precipitate was collected by filtration, rinsed with water, and dried under vacuum. The solid was chromatographed (silica gel, 10% methanol/dichloromethane) to afford 60 mg (29 %) of Example 44 as a yellow solid.

Melting point 129°–132° C. Analysis for $C_{19}H_{21}N_3SO_5\cdot1.18\ H_2O$: 1.0 $CH_2Cl_2$. Calc'd: C, 47.12; H, 5.01; N, 8.24; S, 6.28. Found: C, 47.12; H, 4.87; N, 8.42; S, 5.98.

EXAMPLES 45 to 48

The following examples were prepared as described for Example 3 except that the pH was adjusted to 4–4.5 to precipitate the product from solution. Other differences are listed as: starting material; mL of 5N sodium hydroxide/mmol of starting material; mL of methanol/mmol of staring material; reaction time; reaction temperature; recrystallization solvent; yield.

EXAMPLE 45

6-Amino-N-(3,4-dimethyl-5-isoxazolyl)-1-naphthalenesulfonamide

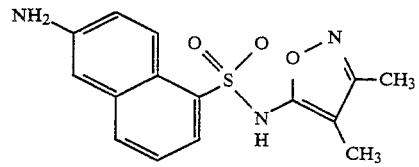

Example 12; 2 mL; 0.4 mL; 17 hours; 70° C.; aqueous methanol; 27%.

Melting point 179°–180° C. Analysis for $C_{15}H_{15}N_3O_3S$ Calc'd: C, 56.44; H, 4.80; N, 13.16; S, 10.04. Found: C, 56.55; H, 4.56; N, 13.05; S, 9.92.

EXAMPLE 46

7-Amino-N-(3,4-dimethyl-5-isoxazolyl)-2-naphthalenesulfonamide

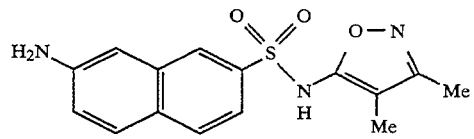

Example 14; 2 mL; 0.7 mL; 3 hours; 80° C.; aqueous ethanol; 75%.

Melting point 193°–194° C. Analysis for $C_{15}H_{15}N_3O_3S\cdot0.07\ H_2O$ Calc'd: C, 56.54; H, 4.79; N, 13.19; S, 10.06. Found: C, 56.78; H, 4.68; N, 13.09; S, 9.73.

EXAMPLE 47

8-Amino-N-(3,4-dimethyl-5-isoxazolyl)-2-naphthalenesulfonamide

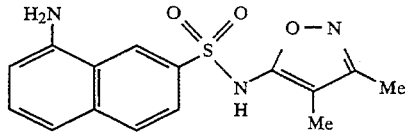

Example 15; 2 mL; 0.4 mL; 3 hours; 80° C.; aqueous ethanol; 70%.

Melting point 198°–202°. Analysis for $C_{15}H_{15}N_3O_3S$ Calc'd: C, 56.77; H, 4.76; N, 13.24; S, 10.10. Found: C, 56.76; H, 4.38; N, 13.12; S, 9.73.

EXAMPLE 48

7-Amino-N-(3,4-dimethyl-5-isoxazolyl)-1-naphthalenesulfonamide

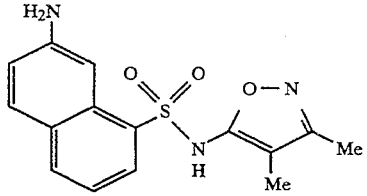

Example 13; 2.8 mL; 1.8 mL; 22 hours; 75° C.; aqueous ethanol; 72%.

Melting point 182°-183° C. Analysis for C15H15N3O3S-0.46 H2O Calc'd: C, 55.32; H, 4.93; N, 12.90; S, 9.84. Found: C, 55.34; H, 4.84; N, 12.78; S, 9.83.

EXAMPLES 49 to 51

The following examples were prepared as described for Example 23, with differences listed as: starting material; equivalents of formaldehyde; equivalents of 3N sulfuric acid; equivalents of sodium cyanoborohydride; reaction time; purification method; yield.

EXAMPLE 49

7-(Dimethylamino)-N-(3,4-dimethyl-5-isoxazolyl)-2-naphthalenesulfonamide

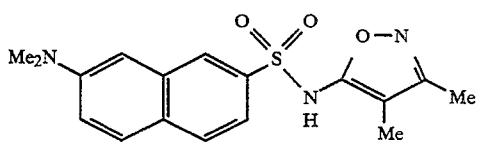

Example 46; 5 equivalents; 1 equivalent; 6 equivalents; 6 hours; flash chromatography on silica with methanol/methylene chloride followed by recrystallization from benzene/hexanes; 36%.

Melting point 131°-132° C. Analysis for C17H19N3O3S-0.4 H2O; 0.4 C6H6 Calc'd: C, 60.70; H, 5.83; N, 10.95; S, 8.35. Found: C, 60.58; H, 5.52; N, 10.84; S, 8.61.

EXAMPLE 50

8-(Dimethylamino)-N-(3,4-dimethyl-5-isoxazolyl)-2-naphthalenesulfonamide

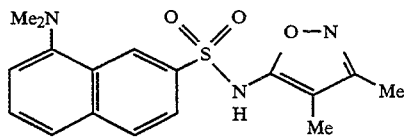

Example 47; 5 equivalents; 1 equivalent; 6 equivalents; 4 hours; flash chromatography on silica with methanol/methylene chloride followed by recrystallization from aqueous ethanol; 49%.

Melting point 155°-156° C. Analysis for C17H19N3O3S-0.13 H2O. Calc'd: C, 58.72; H, 5.58; N, 12.08; S, 9.22. Found: C, 58.76; H, 5.41; N, 12.04; S, 9.45.

EXAMPLE 51

6-(Dimethylamino)-N-(3,4-dimethyl-5-isoxazolyl)-1-naphthalenesulfonamide

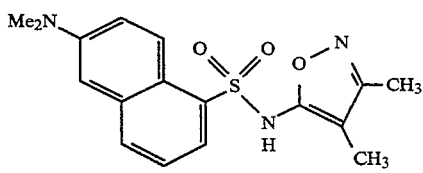

Example 45; 6 equivalents; 1 equivalent; 7 equivalents; 5 hours; flash chromatography on silica with methanol/methylene chloride followed by recrystallization from aqueous ethanol; 15%.

Melting point 182°-183° C. Analysis for C17H19N3O3S. Calc'd: C, 59.11; H, 5.54; N, 12.17; S, 9.28. Found: C, 59.20; H, 5.37; N, 12.05; S, 9.30.

EXAMPLES 52 to 55

The following examples were prepared as described for example 1, with differences listed as: method of reagent combination; reaction time; reaction temperature; purification method; yield.

EXAMPLE 52

5-(Dimethylamino)-N-(3-methyl-4-nitro-5-isoxazolyl)-1-naphthalenesulfonamide

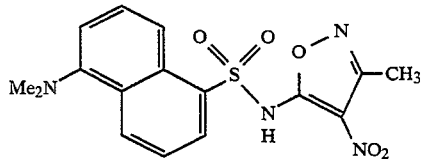

Dropwise; 65 hours; room temperature; precipitation from 5% aqueous sodium hydrogen carbonate; 32%.

Melting point 220°-228° C. Analysis for C16H16N4O5S. Calc'd: C, 50.07; H, 4.42; N, 14.60; S, 8.35. Found: C, 50.45; H, 4.04; N, 14.22; S, 8.14.

EXAMPLE 53

5-(Dimethylamino)-N-(4,5,6,7-tetrahydro-2,1-benzisoxazol-3-yl)-1-naphthalenesulfonamide

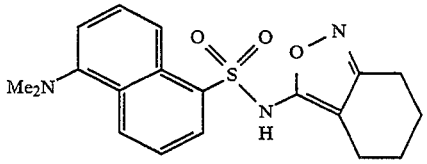

Dropwise; 5 hours; 75° C.; dissolved in ether, filtered, filtrate concentrated; 18%.

Melting point 69°-80° C. Analysis for C19H21N3O3S-0.8 H2O. Calc'd: C, 59.14; H, 5.90; N, 10.89; S, 8.31. Found: C, 59.29; H, 5.74; N, 10.74; S, 8.59.

EXAMPLE 54

5-(Dimethylamino)-N-(4-ethyl-3-methyl-5-isoxazolyl)-1-naphthalenesulfonamide

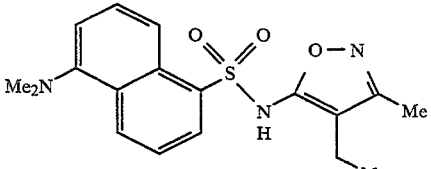

Batchwise; 1 hour; 100° C.; flash chromatography on silica with ethyl acetate/hexanes followed by precipitation from 5% aqueous sodium hydrogen carbonate; 43%.

Melting point 55°-85° C. Analysis for C18H21N3O3S-0.04 H2O. Calc'd: C, 60.03; H, 5.90; N, 11.67; S, 8.90. Found: C, 59.99; H, 6.02; N, 11.71;S, 8.81.

EXAMPLE 55

5-(Dimethylamino)-N-(4-methyl-5-isoxazolyl)-1-naphthalenesulfonamide

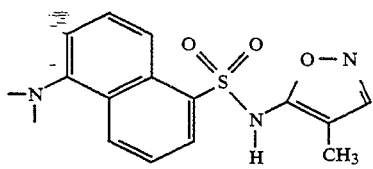

Batchwise; 18 hours; room temperature; flash chromatography on silica with ethyl acetate followed by precipitation from 5% aqueous sodium hydrogen carbonate; 17%.

Melting point 57°–67° C. Analysis for $C_{16}H_{17}N_3O_3S \cdot 0.41H_2O$. Calc'd: C, 56.73; H, 5.30; N, 12.40; S, 9.46. Found: C, 56.51; H, 5.04; N, 12.62; S, 9.34.

EXAMPLE 56

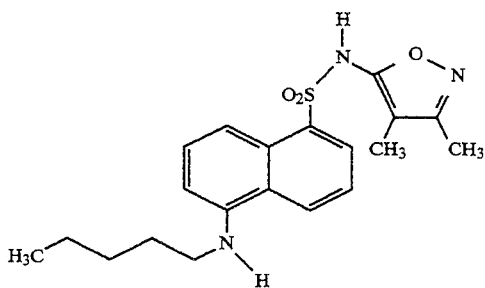

N-(3,4-Dimethyl-5-isoxazolyl)-5-(pentylamino)-1-naphthalenesufonamide

A. N-5-[[(3,4-Dimethyl-5-isoxazolyl)amino]sulfonyl]-1-naphthalenyl]pentanamide

Valeryl chloride (0.32 mL, 2.7 mmol) was added dropwise to a solution of Example 3 (0.68 g, 2.1 mmol) and pyridine (2.0 mL) in acetone (14 mL) under argon and the solution was stirred for 2.5 hours. The acetone was evaporated, half-saturated sodium hydrogen carbonate (60 mL) was added to the residue, and the pH was adjusted to 8–8.5 with saturated sodium hydrogen carbonate. The mixture was stirred for 1 hour, acidified with 6N hydrochloric acid to pH 1.0, and stirred overnight. The solid was collected by filtration, washed with water, and dried. Recrystallization from methanol/water afforded 0.72 g (84%) of compound A, mp 171°–172° C.

B. N-(3,4-Dimethyl-5-isoxazolyl)-amino]sulfonyl-1-naphthalenyl]pentanamide

Compound A (0.71 g, 1.8 mmol) was added to a solution of borane (1.0M in tetrahydrofuran, 5.3 mL, 5.3 mmol) in tetrahydrofuran (37 mL) at 0° C. The solution was stirred at 0° C. for 20 minutes, at ambient temperature for 1 hour, and at reflux for 2 hours. The mixture was evaporated, water was slowly added to the residue, and the mixture was partitioned between water and methylene chloride. The aqueous phase was extracted twice with methylene chloride, and the combined organic phases were dried (magnesium sulfate) and evaporated. Flash chromatography (silica, 3% methanol/methylene chloride) afforded 0.31 g of solid which was recrystallized from methanol/water to afford 0.23 g (33%) of Example 56 as a bright yellow crystalline solid, mp 143°–145° C.

Analysis for $C_{20}H_{25}N_3O_3S$ Calc'd: C, 61.99; H, 6.50; N, 10.84; S, 8.27. Found: C, 62.05; H, 6.54; N, 10.84; S, 7.94.

EXAMPLE 57

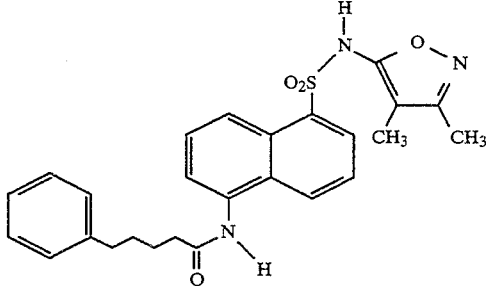

N-[5-[[(3,4-Dimethyl-5-isoxazolyl)amino]sulfonyl]-1-naphthalenyl]-5-benzenepentanamide Example 57 was prepared from 5-phenylvaleroyl chloride and Example 3 as described for compound A from Example 56. Recrystallization from methanol/water afforded an 85% yield of Example 57 as a white crystalline solid, mp 168°–171° C.

Analysis for $C_{26}H_{27}N_3O_4S$ Calc'd: C, 65.39; H, 5.70; N, 8.80; S, 6.71. Found: C, 65.53; H, 5.76; N, 8.91; S, 6.55.

EXAMPLE 58

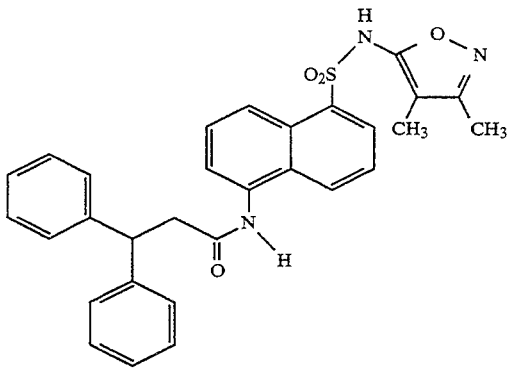

N-[5-[[(3,4-Dimethyl-5-isoxazolyl)amino]sulfonyl]-1-naphthalenyl]-β-phenylbenzenepropanamide Example 58 was prepared from 3,3-diphenylpropanoyl chloride and Example 3 as described for compound A from Example 56. Recrystallization from methanol/water afforded a 72% yield of Example 58 as a white crystalline solid, mp 200°–204° C.

Analysis for $C_{30}H_{27}N_3O_4S \cdot 0.19\ H_2O$ Calc'd: C, 68.10; H, 5.22; N, 7.94; S, 6.06. Found: C, 68.26; H, 5.11; N, 7.78; S, 5.96.

EXAMPLE 59

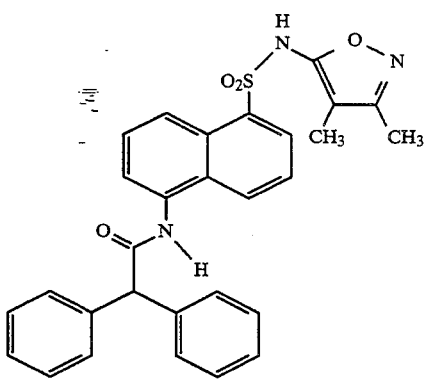

N-[5-[[(3,4-Dimethyl-5-isoxazolyl)amino]sulfonyl]-1-naphthalenyl]-α-phenylbenzeneacetamide Example 59 was prepared from 3,3-diphenylacetyl chloride and Example 3 as described for compound A from Example 56. Recrystallization from methanol/water afforded a 65% yield of Example 59 as a tan crystalline solid, mp 218°–222° C.

Analysis for $C_{29}H_{25}N_3O_4S.0.12$ $H_2O$ Calc'd: C, 67.79; H, 4.95; N, 8.18; S, 6.24. Found: C, 67.88; H, 5.11; N, 8.09; S, 6.29.

EXAMPLE 60

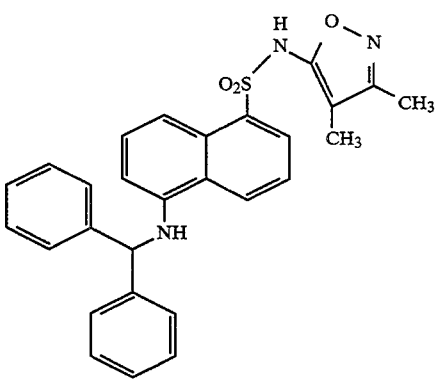

N-(3,4-Dimethyl-5-isoxazolyl)-5-[(diphenylmethyl)amino]-1-naphthalenesufonamide

A. N-(3,4-Dimethyl-5-isoxazolyl)-5-[(diphenylmethylene)amino]-1-naphthalenesulfonamide Concentrated hydrochloric acid (0.36 mL, 4.4 mmol) was added to a solution of Example 3 (1.4 g, 4.4 mmol) in methylene chloride (20 mL) and methanol (8 mL). The solvent was removed and methylene chloride (16 mL) and benzophenone imine (0.83 g, 4.4 mmol) were added. The solution was stirred for 3 days with the exclusion of moisture, and the resulting yellow solid was filtered and rinsed with methylene chloride and water. The organic phase was separated from the filtrate, dried (magnesium sulfate) and evaporated. The residue was recrystallized from methanol, and the crystalline solid was combined with the yellow solid and recrystallized from methanol to afford 1.30 g (66%) of compound A as a yellow crystalline solid, mp 220°–225° C.

B. N-(3,4-Dimethyi-5-isoxazolyl)-5-[(diphenylmethyl)amino]-1-naphthalenesulfonamide Example 60 was prepared from compound A as described for compound B from Example 56. Flash chromatography (silica, 5% methanol/methylene chloride) followed by recrystallization from methanol/water afforded Example 60 as a yellow crystalline solid, mp 152°–158° C.

Analysis for $C_{28}H_{25}N_3O_3S.0.18$ $H_2O$ Calc'd: C, 69.09; H, 5.25; N, 8.63; S, 6.59. Found: C, 69.12; H, 5.14; N, 8.60; S, 6.60.

EXAMPLE 61

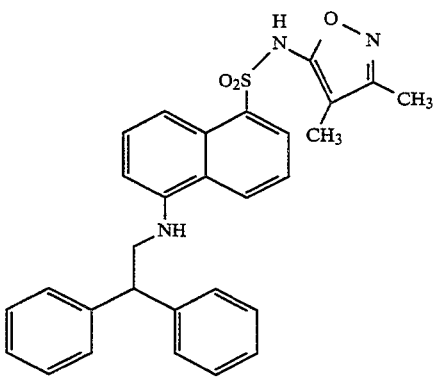

N-(3,4-Dimethyl-5-isoxazolyl)-5-[(2,2-diphenylethyl)amino]-1-naphthalenesufonamide Example 61 was prepared from Example 59 as described for compound B from Example 56. Flash chromatography (silica, 5% methanol/methylene chloride) followed by recrystallization from ethanol/water afforded Example 61 as a yellow crystalline solid, mp 206°–211° C.

Analysis for $C_{29}H_{27}N_3O_3S.0.31$ $H_2O$ Calc'd: C, 69.23; H, 5.53; N, 8.35; S, 6.37. Found: C, 69.25; H, 5.49; N, 8.33; S, 6.24.

EXAMPLE 62

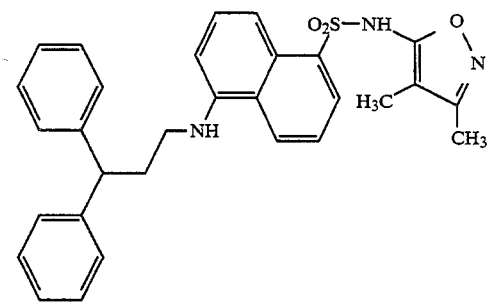

N-(3,4-Dimethyl-5-isoxazolyl)-5-[(3,3-diphenylpropyl)amino]-1-naphthalenesufonamide Example 62 was prepared from Example 58 as described for compound B from Example 56. Flash chromatography (silica, 5% methanol/methylene chloride) followed by recrystallization from ether afforded Example 62 as a yellow crystalline solid, mp 171°–177° C.

Analysis for $C_{30}H_{29}N_3O_3S.0.75$ $H_2O$ Calc'd: C, 68.61; H, 5.85; N, 8.00; S, 6.20. Found: C, 68.77; H, 5.66; N, 7.84; S, 6.10.

EXAMPLE 63

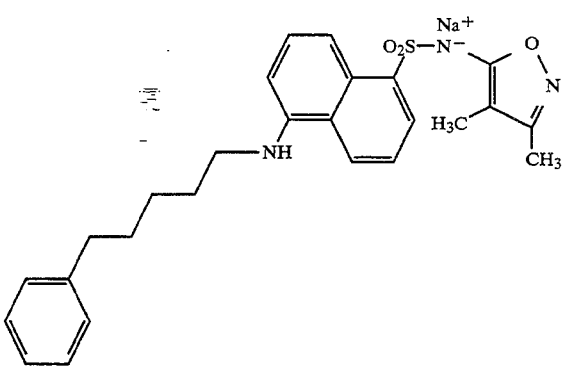

N-(3,4-Dimethyl-5-isoxazolyl)-5-[(5-phenylpentyl)amino]-1-naphthalenesufonamide, sodium salt Example 63 was prepared from Example 48 as described for compound B from Example 57. After flash chromatography (silica, 5% methanol/methylene chloride), the material was dissolved in 5% sodium hydrogen carbonate and added to a 5 g Waters SepPak tC18 cartridge which had been equilibrated with methanol followed by water. The column was eluted with water, 25% methanol/water, 50% methanol/water and methanol. Evaporation of the 50% methanol/water fraction followed by drying on high vacuum afforded Example 63 as a yellow-green glass, mp 120°–123° C.

Analysis for $C_{26}H_{28}N_3O_3SNa.0.72\ H_2O$ Calc'd: C, 62.65; H, 5.95; N, 8.43; S, 6.43. Found: C, 62.74; H, 5.96; N, 8.34; S, 6.37.

EXAMPLE 64

N-(3,4-Dimethyl-5-isoxazolyl)-5-(methylamino)-1-naphthalenesulfonamide

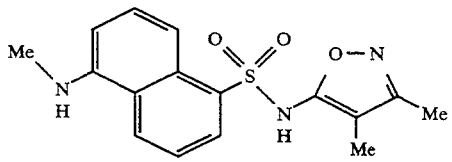

A. N-[5-[[(3,4-Dimethyl-5-isoxazolyl)amino]sulfonyl]-1-naphthalenyl]formamide

Formic acid (95%, 1.90 mL, 50.4 mmol) was added dropwise to acetic anhydride (3.90 mL, 41.0 mmol) at 0° C. The mixture was heated at 55° C. for 2 hours, cooled to room temperature and diluted with tetrahydrofuran (9 mL). A solution of Example 3 (5.00 g, 15.8 mmol) in tetrahydrofuran (10 mL) was added dropwise and the mixture was stirred at room temperature for 30 minutes and concentrated. The residue was diluted with water (200 mL) and methanol (100 mL), and 5N sodium hydroxide was added in 2-mL portions to keep the pH of the solution between 9 and 11. After the solids had dissolved and the pH remained at 11, the mixture was stirred for 10 minutes and was brought to pH 8 with aqueous hydrochloric acid. The methanol was evaporated, water (200 mL) was added to the residue and the pH was brought to 3 with 6N hydrochloric acid. The mixture was stirred vigorously to break up lumps and the solid was collected by filtration, washed with water (3×20 mL) and dried to provide 5.05 g of compound A as a white-pink powder (93%).

B. N-(3,4-Dimethyl-5-isoxazolyl)-5-(methylamino)-1-naphthalenesulfonamide

To a solution at 0° C. of compound A (5.00 g, 14.5 mmol) in tetrahydrofuran (100 mL) was added dropwise boranemethylsulfide (5.8 mL, 57.9 mmol). The mixture was stirred at 0° C. for 10 minutes and at reflux for 3 hours, cooled to 0° C., and methanol (40 mL) was added. After hydrogen evolution slowed, the mixture was brought to room temperature, stirred for 40 minutes, and concentrated aqueous hydrochloric acid was added to bring the pH to 2–2.5. The mixture was heated at reflux for 40 minutes, the solvent was evaporated, the residue was taken up in water (200 mL) and the pH of this solution was adjusted to 3 with aqueous hydrochloric acid. The resulting precipitate was collected by filtration, dried, and chromatographed (silica, 50% ethyl acetate/hexanes). The product was dissolved in 5% sodium bicarbonate (100 mL), the solution was filtered through Celite, the filtrate was diluted with water (200 mL) and the pH of the filtrate was adjusted to 3 with 6N hydrochloric acid. The resulting precipitate was collected by filtration, washed with water (2×50 mL) and dried to provide Example 64 as a yellow solid (3.30 g, 69%), mp 188°–191° C.

Analysis for $C_{16}H_{17}N_3O_3S.0.62\ H_2O$ Calc'd: C, 56.09; H, 5.37; N, 12.26; S, 9.36. Found: C, 56.23; H, 5.34; N, 12.12; S, 9.27.

What is claimed is:

1. A compound of the formula

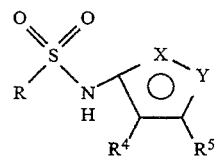

or a pharmaceutically acceptable salt thereof, wherein:
one of X and Y is N and the other is O;
R is naphthyl or naphthyl substituted with $R^1$, $R^2$ and $R^3$;
$R^1$, $R^2$ and $R^3$ are each independently
 (a) hydrogen;
 (b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
 (c) halo;
 (d) hydroxyl;
 (e) cyano;
 (f) nitro;
 (g) —C(O)H or —C(O)$R^6$;
 (h) —CO$_2$H or —CO$_2R^6$;
 (i) —SH, —S(O)$_nR^6$, —S(O)$_m$—OH, —S(O)$_m$—O$R^6$, —O—S(O)$_m$—$R^6$, —O—S(O)$_m$OH, or —O—S(O)$_m$—O$R^6$;
 (j) —$Z^4$—N$R^7R^8$; or
 (k) —$Z^4$—N($R^{11}$)—$Z^5$—N$R^9R^{10}$;
$R^4$ and $R^5$ are each independently
 (a) hydrogen;
 (b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
 (c) halo;

(d) hydroxyl;
(e) cyano;
(f) nitro;
(g) —C(O)H or —C(O)$R^6$;
(h) —$CO_2H$ or —$CO_2R^6$;
(i) —SH, —S(O)$_n R^6$, —S(O)$_m$—OH, —S(O)$_m$—O$R^6$, —O—S(O)$_m$—$R^6$, —O—S(O)$_m$OH, or —O—S(O)$_m$—O$R^6$;
(j) —$Z^4$—$NR^7R^8$;
(k) —$Z^4$—N($R^{11}$)—$Z^5$—$NR^9R^{10}$; or
(l) $R^4$ and $R^5$ together are alkylene or alkenylene (either of which may be substituted with $Z^1$, $Z^2$ and $Z^3$), completing a 4- to 8-membered saturated, unsaturated or aromatic ring together with the carbon atoms to which they are attached;

$R^6$ is alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^7$ is
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;
(c) cyano;
(d) hydroxyl;
(e) —C(O)H or —C(O)$R^6$;
(f) —$CO_2H$ or —$CO_2R^6$;
(g) —SH, —S(O)$_n R^6$, —S(O)$_m$—OH, —S(O)$_m$—O$R^6$, —O—S(O)$_m$—$R^6$, —O—S(O)$_m$OH, or —O—S(O)$_m$—O$R^6$, except when $Z^4$ is —S(O)$_n$—;

$R^8$ is
(a) hydrogen;
(b) —C(O)H or —C(O)$R^6$, except when $Z^4$ is —C(O)— and $R^7$ is —C(O)H, —C(O)$R^6$, —$CO_2H$, or —$CO_2R^6$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$; or $R^7$ and $R^8$ together are alkylene or alkenylene (either of which may be substituted with $Z^1$, $Z^2$ and $Z^3$), completing a 3- to 8-membered saturated, unsaturated or aromatic ring together with the nitrogen atom to which they are attached;

$R^9$ is
(a) hydrogen;
(b) hydroxyl;
(c) —C(O)H or —C(O)$R^6$;
(d) —$CO_2H$ or —$CO_2R^6$;
(e) —SH, —S(O)$_n R^6$, —S(O)$_m$—OH, —S(O)$_m$—O$R^6$, —O—S(O)$_m$—$R^6$, —O—S(O)$_m$OH, or —O—S(O)$_m$—O$R^6$;
(f) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^{10}$ is
(a) hydrogen;
(b) —C(O)H or —C(O)$R^6$, except when $Z^5$ is —C(O)— and $R^9$ is —C(O)H, —C(O)$R^6$, —$CO_2H$, or —$CO_2R^6$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

$R^{11}$ is
(a) hydrogen;
(b) hydroxyl, $CO_2R^6$ or $CO_2H$, except when one of $R^9$ and $R^{10}$ is hydroxyl, $CO_2R^6$ or $CO_2H$;
(c) —C(O)H or —C(O)$R^6$; or
(d) alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$;

or any two of $R^9$, $R^{10}$ and $R^{11}$ together are alkylene or alkenylene (either of which may be substituted with $Z^1$, $Z^2$ and $Z^3$), completing a 3- to 8-membered saturated, unsaturated or aromatic ring together with the atoms to which they are attached;

$Z^1$, $Z^2$ and $Z^3$ are each independently
(a) hydrogen;
(b) halo;
(c) hydroxy;
(d) alkoxy;
(e) —SH, —S(O)$_n Z^6$, —S(O)$_m$—OH, —S(O)$_m$—O$Z^6$, —O—S(O)$_m$—$Z^6$, —O—S(O)$_m$OH, or —O—S(O)$_m$—O$Z^6$;
(f) oxo;
(g) nitro;
(h) cyano;
(i) —C(O)H or —C(O)$Z^6$;
(j) —$CO_2H$ or —$CO_2Z^6$; or
(k) —$NZ^7Z^8$, —C(O)$NZ^7Z^8$, or —S(O)$_n Z^7Z^8$;

$Z^4$ and $Z^5$ are each independently
(a) a single bond;
(b) —S(O)$_n$—;
(c) —C(O)—;
(d) —C(S)—; or
(e) alkyl, alkenyl, alkynyl, cycloalkyl, cycloalkylalkyl, cycloalkenyl, cycloalkenylalkyl, aryl, or aralkyl, any of which may be substituted with $Z^1$, $Z^2$ and $Z^3$;

$Z^6$, $Z^7$ and $Z^8$ are each independently hydrogen, alkyl, alkenyl, alkynyl, cycloalkyl, cycloalkylalkyl, cycloalkenyl, cycloalkenylalkyl, aryl, or aralkyl, or $Z^7$ and $Z^8$ together are alkylene or alkenylene, completing a 3- to 8-membered saturated, unsaturated or aromatic ring together with the nitrogen atom to which they are attached;

m is 1 or 2; and
n is 0, 1, or 2.

2. The compound of claim 1, wherein one of $R^1$, $R^2$ and $R^3$ is —$NR^7R^8$.

3. The compound of claim 2, wherein $R^7$ and $R^8$ are each independently hydrogen, alkyl, or C(O)alkyl.

4. The compound of claim 1, wherein R is

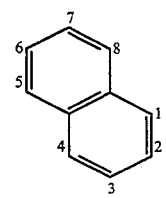

with the sulfonamide attached at position 1 or 2 and one of $R^1$, $R^2$, and $R^3$ attached at position 5 or 6.

5. The compound of claim 4, wherein one of $R^1$, $R^2$ and $R^3$ is —$NR^7R^8$.

6. The compound of claim 5, wherein $R^7$ and $R^8$ are each independently hydrogen, alkyl, or C(O)alkyl.

7. The compound of claim 6, wherein $R^7$ and $R^8$ are each independently hydrogen, methyl, methylethyl or acetyl.

8. The compound of claim 1, having the formula

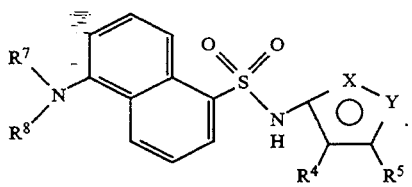

9. The compound of claim 8, wherein $R^7$ and $R^8$ are each independently hydrogen, alkyl, or C(O)alkyl.

10. The compound of claim 9, wherein $R^7$ and $R^8$ are each independently hydrogen, methyl, methylethyl or acetyl.

11. The compound of claim 1, wherein $R^4$ and $R^5$ are alkyl.

12. The compound of claim 4, wherein $R^4$ and $R^5$ are alkyl.

13. The compound of claim 1, wherein $R^4$ and $R^5$ are methyl.

14. The compound of claim 4, wherein $R^4$ and $R^5$ are methyl.

15. The compound of claim 1, selected from the group consisting of:

5-(Dimethylamino)-N-(3,4-dimethyl-5-isoxazolyl)-1-naphthalenesulfonamide;
N-[5-[[(3,4-Dimethyl-5-isoxazolyl)amino]sulfonyl]-1-naphthalenyl]acetamide;
5-Amino-N-(3,4-dimethyl-5-isoxazolyl)-1-naphthalenesulfonamide;
N-[6-[[(3,4-dimethyl-5-isoxazolyl)amino]sulfonyl]-1-naphthalenyl]acetamide;
5-Amino-N-(3,4-dimethyl-5-isoxazolyl)-2-naphthalenesulfonamide;
N-[4-[[(3,4-Dimethyl-5-isoxazolyl)amino]sulfonyl]-1-naphthalenyl]acetamide;
N-[6-[[(3,4-Dimethyl-5-isoxazolyl)amino]sulfonyl]-2-naphthalenyl]acetamide;
6-Amino-N-(3,4-dimethyl-5-isoxazolyl)-2-naphthalenesulfonamide;
4-Amino-N-(3,4-dimethyl-5-isoxazolyl)-1-naphthalenesulfonamide;
5-Dimethylamino-N-(4,5-dimethyl-3-isoxazolyl)-1-naphthalenesulfonamide;
N-[5-[[(4,5-dimethyl-3-isoxazolyl)amino]sulfonyl]-1-naphthalenyl]acetamide;
N-[5-[[(3,4-dimethyl-5-isoxazolyl)amino]sulfonyl]-2-naphthalenyl]acetamide;
N-[8-[[(3,4-dimethyl-5-isoxazolyl)amino]sulfonyl]-2-naphthalenyl]acetamide;
N-[7-[[(3,4-dimethyl-5-isoxazolyl)amino]sulfonyl]-2-naphthalenyl]acetamide;
N-[7-[[(3,4-dimethyl-5-isoxazolyl)amino]sulfonyl]-1-naphthalenyl]acetamide;
N-(3,4-Dimethyl-5-isoxazolyl)-5-methoxy-1-naphthalenesulfonamide;
N-(3,4-Dimethyl-5-isoxazolyl)-1-napthalenesulfonamide;
5-[(1-Methylethyl)amino ]-N-(3,4-dimethyl-5-isoxazolyl)-1-naphthalenesulfonamide;
N-[5-[[(3,4-Dimethyl-5-isoxazolyl)amino]sulfonyl]-1-naphthalenyl]-2-methylpropanamide;
5-Chloro-N-(3,4-dimethyl-5-isoxazolyl)-1-naphthalenesulfonamide;
N-(3,4-Dimethyl-5-isoxazolyl)-5-[(phenylmethyl)amino]-1-naphthlenesulfonamide;
N-(3,4-Dimethyl-5-isoxazolyl)-5-hydroxy-1-naphthalenesulfonamide;
7-(Dimethylamino)-N-(3,4-dimethyl-5-isoxazolyl)-1-naphthalenesulfonamide;
N-(3,4-Dimethyl-5-isoxazolyl)-5-[methyl(1-methylethyl)amino]-1-naphthalenesulfonamide;
2-[[5-[[(3,4-Dimethyl-5-isoxazolyl)amino]sulfonyl]-1-naphthalenyl]amino]propanoic acid, ethyl ester
N-(3,4-Dimethyl-5-isoxazolyl)-5-(2-oxo-1-pyrrolidinyl)-1-naphthalenesulfonamide;
N-(3,4-Dimethyl-5-isoxazolyl)-5-(2-oxo-1-piperidinyl)-1-naphthalenesulfonamide;
N-(3,4-Dimethyl-5-isoxazolyl)-5-[[(phenylamino)thioxomethyl]amino]-1-naphthalenesulfonamide;
N-(3,4-Dimethyl-5-isoxazolyl)-5-(1-pyrrolidinyl)-1-naphthalenesulfonamide;
5-[[(3,4-Dimethyl-5-isoxazolyl)amino]sulfonyl]-1-naphthalenecarboxylic acid;
5-[[[5-(Dimethylamino)-1-naphthalenyl]sulfonyl]amino]-3-methyl-4-isoxazolecarboxylic acid, ethyl ester;
5-[[(3,4-Dimethyl-5-isoxazolyl)amino]sulfonyl]-1-naphthalenecarboxylic acid, methyl ester;
5-(Dimethylamino)-N-(3-methyl-5-isoxazolyl)-1-naphthalenesulfonamide;
5-[(Dimethylamino)methyl]-N-(3,4-dimethyl-5-isoxazolyl)-1-naphthalenesulfonamide, trifluoroacetate (1:1) salt;
N-(3,4-Dimethyl-5-isoxazolyl)-5-(1-hydroxy-1-methylethyl)-1-naphthalenesulfonamide;
N-(3,4-Dimethyl-5-isoxazolyl)-5-(1-methylethenyl)-1-naphthalenesulfonamide;
N-(3,4-Dimethyl-5-isoxazolyl)-5-(1-piperidinyl)-1-naphthalenesulfonamide, trifluoroacetate (2:1) salt;
N-(3,4-Dimethyl-5-isoxazolyl)-5-(methylamino)-1-naphthalenesulfonamide;
N-(3,4-Dimethyl-5-isoxazoyl)-5-(ethylamino)-1-naphthalenesulfonamide;
N-(3-Methyl-4-phenylmethyl-5-isoxazolyl)-5-[dimethylamino]-1-naphthalenesulfonamide;
N-(3-Methyl-4-phenyl-5-isoxazolyl)-5-(dimethylamino)-1-naphthalenesulfonamide;
N-(3-Ethyl-4-methyl-5-isoxazolyl)-5-(dimethylamino )-1-naphthalenesulfonamide;
5-(Dibutylamino)-N-(3,4-dimethyl-5-isoxazolyl)-1-naphthalenesulfonamide, monosodium salt;
4-[1-[[(3,4-Dimethyl-5-isoxazolyl)amino]sulfonyl]naphthalen-5-yl]amino]butanoic acid;
6-Amino-N-(3,4-dimethyl-5-isoxazolyl)-1-naphthalenesulfonamide;
7-Amino-N-(3,4-dimethyl-5-isoxazolyl)-2-naphthalenesulfonamide;
8-Amino-N-(3,4-dimethyl-5-isoxazolyl)-2-naphthalenesulfonamide;
7-Amino-N-(3,4-dimethyl-5-isoxazolyl)-1-naphthalenesulfonamide;
7-(Dimethylamino)-N-(3,4-dimethyl-5-isoxazolyl)-2-naphthalenesulfonamide;
8-(Dimethylamino)-N-(3,4-dimethyl-5-isoxazolyl)-2-naphthalenesulfonamide;
6-(Dimethylamino)-N-(3,4-dimethyl-5-isoxazolyl)-1-naphthalenesulfonamide;
5-(Dimethylamino)-N-(3-methyl-4-nitro-5-isoxazolyl)-1-naphthalenesulfonamide;

5-(Dimethylamino)-N-(4,5,6,7-tetrahydro-2,1-benzisoxazol-3-yl)-1-naphthalenesulfonamide;

5-(Dimethylamino)-N-(4-ethyl-3-methyl-5-isoxazolyl)-1-naphthalenesulfonamide;

5-(Dimethylamino)-N-(4-methyl-5-isoxazolyl)-1-naphthalenesulfonamide;

N-(3,4-Dimethyl-5-isoxazolyl)-5-(pentylamino)-1-naphthalenesufonamide;

N-[5-[[(3,4-Dimethyl-5-isoxazolyl)amino]sulfonyl]-1-naphthalenyl]-5-benzenepentanamide;

N-[5-[[(3,4-Dimethyl-5-isoxazolyl)amino]sulfonyl]-1-naphthalenyl]-β-phenylbenzenepropanamide;

N-[5-[[(3,4-Dimethyl-5-isoxazolyl)amino]sulfonyl]-1-naphthalenyl]-α-phenylbenzeneacetamide;

N-(3,4-Dimethyl-5-isoxazolyl)-5-[(diphenylmethyl)amino]-1-naphthalenesufonamide;

N-(3,4-Dimethyl-5-isoxazolyl)-5-[(2,2-diphenylethyl)amino]-1-naphthalenesufonamide;

N-(3,4-Dimethyl-5-isoxazolyl)-5-[(3,3-diphenylpropyl)amino]-1-naphthalenesufonamide; and N-(3,4-Dimethyl-5-isoxazolyl)-5-[(5-phenylpentyl)amino]-1-naphthalenesufonamide, sodium salt.

16. A method of treating endothelin-related disorders in a mammal, which comprises administering an effective amount of a compound of claim 1.

17. A method of treating hypertension, which comprises administering an effective amount of a compound of claim 1.

18. A method of treating renal, glomerular or mesangial cell disorders, which comprises administering an effective amount of a compound of claim 1.

19. A method of treating endotoxemia, which comprises administering an effective amount of a compound of claim 1.

20. A method of treating ischemia, which comprises administering an effective amount of a compound of claim 1.

* * * * *